United States Patent
Bui et al.

(10) Patent No.: US 7,690,259 B2
(45) Date of Patent: Apr. 6, 2010

(54) INTEGRATED ULTRASONIC INSPECTION PROBES, SYSTEMS, AND METHODS FOR INSPECTION OF COMPOSITE ASSEMBLIES

(75) Inventors: Hien T. Bui, Auburn, WA (US); Fred D. Young, Bellevue, WA (US); Mark A. Lee, Kent, WA (US); Richard C. Krotzer, Enumclaw, WA (US); Clyde T. Uyehara, Kent, WA (US); Barry A. Fetzer, Renton, WA (US)

(73) Assignee: The Boeing Company, Chicago, IL (US)

(*) Notice: Subject to any disclaimer, the term of this patent is extended or adjusted under 35 U.S.C. 154(b) by 143 days.

(21) Appl. No.: 12/263,537

(22) Filed: Nov. 3, 2008

(65) Prior Publication Data

US 2009/0133500 A1 May 28, 2009

Related U.S. Application Data

(63) Continuation of application No. 11/477,686, filed on Jun. 29, 2006, now Pat. No. 7,464,596, which is a continuation-in-part of application No. 11/368,557, filed on Mar. 6, 2006, which is a continuation-in-part of application No. 11/213,652, filed on Aug. 26, 2005, now Pat. No. 7,444,876, and a continuation-in-part of application No. 10/949,625, filed on Sep. 24, 2004, now Pat. No. 7,254,519, and a continuation-in-part of application No. 11/178,584, filed on Jul. 11, 2005, and a continuation-in-part of application No. 11/178,637, filed on Jul. 11, 2005, now Pat. No. 7,337,673.

(51) Int. Cl.
*G01N 29/26* (2006.01)
*G01N 29/28* (2006.01)

(52) U.S. Cl. ............................. 73/625; 73/620; 73/640; 73/641; 73/644; 73/866.5

(58) Field of Classification Search ................ 73/625, 73/618, 620, 635, 640, 641, 644, 866.5
See application file for complete search history.

(56) References Cited

U.S. PATENT DOCUMENTS 3,534,591 A  10/1970 Phelan (Continued)

FOREIGN PATENT DOCUMENTS

DE  28 31 395 A1  1/1980

(Continued)

OTHER PUBLICATIONS

*Maxim CMOS RF/Video Multiplexers*, MAX310/311, Maxim Integrated Products, (undated), available at http://pdfserv.maxim-ic.com/en/ds/MAX310-MAX311.pdf (Sep. 24, 2004), 7 pages.

(Continued)

*Primary Examiner*—J M Saint Surin
(74) *Attorney, Agent, or Firm*—Alston & Bird LLP

(57) ABSTRACT

Apparatus, systems, and methods for inspecting a structure are provided which permit inspection of uniquely shaped structures such as fuselage frames and shear ties. Probes may be constructed from rapid prototyping. Inspection may be performed manually and may use a portable function support system for delivering fluid couplant, controlling transmit and receive functions of the inspection sensors, and delivering immediate visual analysis for an operator. Integrated ultrasonic inspection apparatus, systems, and methods facilitate fast and efficient custom inspection devices and inspecting otherwise difficult-to-inspect structures.

36 Claims, 14 Drawing Sheets

U.S. PATENT DOCUMENTS

| | | | |
|---|---|---|---|
| 3,575,042 A | 4/1971 | Lovelace et al. | |
| 3,789,350 A | 1/1974 | Rolle | |
| 3,809,607 A | 5/1974 | Murray et al. | |
| 3,810,384 A * | 5/1974 | Evans | 73/611 |
| 3,958,451 A | 5/1976 | Richardson | |
| 4,010,636 A | 3/1977 | Clark et al. | |
| 4,103,234 A | 7/1978 | Frazier, Jr. | |
| 4,112,850 A * | 9/1978 | Sigel-Gfeller | 104/138.2 |
| 4,117,733 A | 10/1978 | Gugel | |
| 4,160,386 A | 7/1979 | Jackson et al. | |
| 4,167,880 A | 9/1979 | George | |
| 4,173,897 A | 11/1979 | Förstermann et al. | |
| 4,173,898 A | 11/1979 | Förstermann et al. | |
| 4,229,796 A | 10/1980 | Garrett | |
| 4,311,052 A | 1/1982 | Jeffras et al. | |
| 4,327,588 A | 5/1982 | North | |
| 4,365,514 A | 12/1982 | Ho | |
| 4,368,644 A | 1/1983 | Wentzell et al. | |
| 4,399,703 A | 8/1983 | Matzuk | |
| 4,466,286 A | 8/1984 | Berbeé et al. | |
| 4,470,304 A | 9/1984 | Nusbickel, Jr. et al. | |
| 4,474,064 A | 10/1984 | Naruse et al. | |
| 4,495,587 A | 1/1985 | Plante et al. | |
| 4,559,825 A | 12/1985 | Martens | |
| 4,612,808 A | 9/1986 | McKirdy et al. | |
| 4,752,895 A | 6/1988 | Sarr | |
| 4,755,953 A | 7/1988 | Geithman et al. | |
| 4,774,842 A | 10/1988 | Kollar | |
| 4,803,638 A | 2/1989 | Nottingham et al. | |
| 4,807,476 A | 2/1989 | Cook et al. | |
| 4,848,159 A | 7/1989 | Kennedy et al. | |
| 4,868,798 A * | 9/1989 | Fasnacht et al. | 367/104 |
| 4,912,411 A | 3/1990 | Allison et al. | |
| 4,976,150 A | 12/1990 | Deka | |
| 5,007,291 A | 4/1991 | Walters et al. | |
| 5,047,771 A | 9/1991 | Engeler et al. | |
| 5,050,703 A | 9/1991 | Graff et al. | |
| 5,062,301 A | 11/1991 | Aleshin et al. | |
| 5,148,414 A | 9/1992 | Graff et al. | |
| 5,164,921 A | 11/1992 | Graff et al. | |
| 5,241,135 A | 8/1993 | Fetzer | |
| 5,396,890 A | 3/1995 | Weng | |
| 5,417,218 A | 5/1995 | Spivey et al. | |
| 5,421,203 A | 6/1995 | Graff et al. | |
| 5,485,084 A | 1/1996 | Duncan et al. | |
| 5,505,089 A * | 4/1996 | Weigel | 73/635 |
| 5,535,628 A | 7/1996 | Rutherford | |
| 5,567,881 A | 10/1996 | Myers | |
| 5,585,564 A | 12/1996 | Brunty et al. | |
| 5,593,633 A | 1/1997 | Dull et al. | |
| 5,621,414 A | 4/1997 | Nakagawa | |
| 5,625,148 A * | 4/1997 | Rutherford | 73/618 |
| 5,677,490 A | 10/1997 | Gunther et al. | |
| 5,698,787 A | 12/1997 | Parzuchowski et al. | |
| 5,786,535 A | 7/1998 | Takeuchi et al. | |
| 5,902,935 A | 5/1999 | Georgeson et al. | |
| 5,963,882 A | 10/1999 | Viertl et al. | |
| 5,986,549 A | 11/1999 | Teodorescu | |
| 6,057,927 A | 5/2000 | Levesque et al. | |
| 6,138,115 A * | 10/2000 | Agrawal et al. | 707/3 |
| 6,167,110 A | 12/2000 | Possin et al. | |
| 6,167,760 B1 | 1/2001 | Brunty et al. | |
| 6,220,099 B1 | 4/2001 | Marti et al. | |
| 6,474,164 B1 | 11/2002 | Mucciardi et al. | |
| 6,484,583 B1 | 11/2002 | Chennell et al. | |
| 6,507,635 B2 | 1/2003 | Birdwell et al. | |
| 6,516,668 B2 | 2/2003 | Havira et al. | |
| 6,641,535 B2 | 11/2003 | Buschke et al. | |
| 6,658,939 B2 | 12/2003 | Georgeson et al. | |
| 6,711,235 B2 | 3/2004 | Galish et al. | |
| 6,722,202 B1 | 4/2004 | Kennedy et al. | |
| 6,725,721 B2 | 4/2004 | Venczel | |
| 6,748,791 B1 | 6/2004 | Georgeson et al. | |
| 6,772,635 B1 | 8/2004 | Sale et al. | |
| 6,829,959 B2 | 12/2004 | Gifford et al. | |
| 6,839,636 B1 | 1/2005 | Sunshine et al. | |
| 6,843,130 B2 | 1/2005 | Georgeson | |
| 6,843,131 B2 | 1/2005 | Graff et al. | |
| 6,843,312 B2 | 1/2005 | Burk et al. | |
| 6,848,312 B2 | 2/2005 | Georgeson | |
| 6,895,079 B2 | 5/2005 | Birdwell et al. | |
| 6,927,560 B2 | 8/2005 | Pedigo et al. | |
| 6,931,931 B2 | 8/2005 | Graff et al. | |
| 7,050,535 B2 | 5/2006 | Georgeson et al. | |
| 7,055,389 B2 | 6/2006 | Mueller | |
| 7,064,332 B2 | 6/2006 | Favro et al. | |
| 7,228,741 B2 | 6/2007 | Georgeson et al. | |
| 7,231,826 B2 | 6/2007 | Bossi et al. | |
| 7,240,556 B2 | 7/2007 | Georgeson et al. | |
| 7,249,512 B2 | 7/2007 | Kennedy et al. | |
| 7,253,908 B2 | 8/2007 | Vaccaro et al. | |
| 7,263,889 B2 | 9/2007 | Kennedy et al. | |
| 2004/0237653 A1 | 12/2004 | Graff et al. | |
| 2007/0044563 A1 | 3/2007 | Sarr et al. | |
| 2007/0044564 A1 | 3/2007 | Bui et al. | |

FOREIGN PATENT DOCUMENTS

| | | |
|---|---|---|
| DE | 28 52 560 B1 | 1/1980 |
| DE | 44 31 625 C1 | 9/1994 |
| DE | 198 26 759 C1 | 12/1999 |
| DE | 100 43 199 A1 | 9/2002 |
| EP | 1 193 491 A2 | 4/2002 |
| JP | 62-245153 A | 4/1986 |
| JP | 5-346487 A | 12/1993 |
| JP | 09 264877 A | 10/1997 |

OTHER PUBLICATIONS

*24-Bit Dual-Axis Quadrature Counter*, LS7266R1, LSI Computer Systems, Inc., May 2004, available at http://me.in-berlin.de/~urmel/robot/docu/LS7266R1.pdf (Sep. 24, 2004), 14 pages.

*Fast Technologies for Ultrasonic Non Destructive Evaluation—Analog Modules*, Oct. 1997, http://www.iai.csic.es/users/end/am.html available Jul. 16, 2004, 3 pages.

*MS-8 Multiplexer for Multichannel Ultrasonic Testing*, Technical Information, AGFA Krautkramer Ultrasonic Systems, Jun. 2002, 2 pages.

*USIP 20 GP The Ultrasonic Systems Instrument for Automated Testing*, Krautkrämer, Jun. 1994, 12 pages.

*MUX D Multiplexer for Multichannel Ultrasonic Testing*, Krautkramer, Jul. 1998, 2 pages.

*TTUO2-MUX Standalone/Rack*, Fractional T1, 2 or 4 Port Multiplexer, available at http://www.megatelindustries.com/ttu02_mux.pdf (Sep. 24, 2004), 2 pages.

*MUX 8 Ultrasonic Systems Multiplexer*, Ultrasonic Sciences Ltd., Jun. 1998, 2 pages.

*High Speed Large Area Scanning Using Air-Coupled Ultrasound*, J. O. Strycek et al., http://www.qmi-inc.com/High%20Speed%20Large%20Area%20Scanning%20using%20... available Jul. 12, 2004, 5 pages.

*Multi-Channel Multiplexer*, GE Inspection Technologies, http://www.geinspectiontechnologies.com/products/Ultrasonics/Multiplexers/index.html available Aug. 30, 2004, 3 pages.

*Ultrasonics*, GE Inspection Technologies, http://www.geinspectiontechnologies.com/products/Ultrasonics/index.html available Aug. 03, 2004, 1 page.

*Ultrasonic Systems and Testing Machines*, GE Inspection Technologies, http://www.geinspectiontechnologies.com/solutions/TestingMachines/Ultrasonics/index.h... available Aug. 3, 2004, 3 pages.

*RapidScan Rapid C-Scanning*, NDT Solutions, Ltd., http://www.ndtsolutions.com/rscan.htm available Aug. 5, 2004, 2 pages.

*Rapid Scan Specification*, NDT Solutions Ltd., http://www.ndtsolutions.com/spec_rscan.htm, Aug. 5, 2004, 3 pages.

*Mechanical Engineering*, http://www.fen.bris.ac.uk/faculty/publicityapril04brief/page20.html available Aug. 5, 2004, 2 pages.

*Integrated Ultrasonic Arrays for Rapid Manual Inspection and Mapping*, D. Lines, http://www.diagnosticsonar.com/english/industrial/publications/rapidarray.html available Aug. 5, 2004, 17 pages.

*SWIM*, http://www.wavesinsolids.com/intelligent_ultrasonics.htm, available Sep. 24, 2004, 4 pages.

U.S. Appl. No. 10/943,088, filed Sep. 16, 2004; Inventors: Georgeson, entitled *Magnetically Attracted Inspecting Apparatus and Method Using a Ball Bearing*.

U.S. Appl. No. 10/943,135, filed Sep. 16, 2004, Inventors: Georgeson, entitled *Magnetically Attracted Inspecting Apparatus and Method Using a Fluid Bearing*.

U.S. Appl. No. 11/041,499, filed Jan. 24, 2005, Inventors: Kennedy, entitled *Non-Destructive Stringer Inspection Apparatus and Method*.

Stereolithography Made Easy, *What is Rapid Prototyping?*, available at http://www.stereolithography.com/rapidprototyping.php, May 23, 2005, 11 pages.

GE Inspection Technologies: Array Transducers, *Ultrasonic Array Probes*, available at http://www.geinspectiontechnologies.com/products/Ultrasonics/IndustrialProbes/aplparrays.html, dated Mar. 24, 2005, 2 pages.

*Linear Arrays*, available at http://www.ob-ultrasound.net/lineararrays.html, dated Mar. 24, 2005, 2 pages.

U.S. Appl. No. 10/752,890; filed Jan. 7, 2004; In re: Bossi et al.; entitled *Non-Destructive Inspection Device for Inspection Limited-Access Features of a Structure*.

U.S. Appl. No. 11/178,637; filed Jul. 11, 2005; in re: Kennedy et al.; entitled *Ultrasonic Array Probe Apparatus, System, and Method for Traveling Over Holes and Off Edges of a Structure*.

Fischertechnik, Pneumatic Robots, Pneumatic Information; http://www.mbhs.edu/~josborn/palmbot/Info_eng.pdt, available Oct. 10, 2005, pp. 1-5.

FANUC robotics, R-2000iA Series: http://www.fanucrobotics.com/file_repository/fanucmain/R-2000iA%20Series.pdf, available Oct. 10, 2005, 4 pages.

ABB IRB 6600: http://www.abb.co.in/global/inabb/inabb509.nsf/0/579e92967cad8bd16525703b00306b3e/$file/Robotics+IRB6600.pdf; available Oct. 10, 2005, 2 pages.

*CL—Concentric Lock—Pillow Blocks*, http://www.qmbearing.com/CLPillowBlock.html; available Apr. 6, 2005; 2 pages.

*Airpel Anti-Stiction Cylinders*; http://www.airpot.com/beta/html/airpel.html; available Apr. 11, 2005, 2 pages.

\* cited by examiner

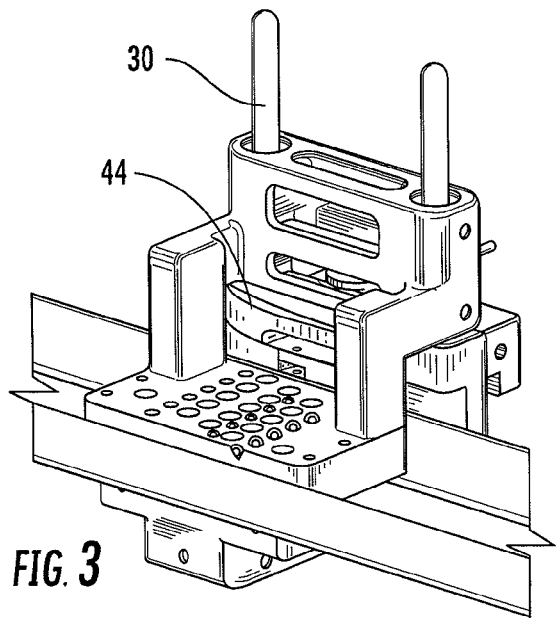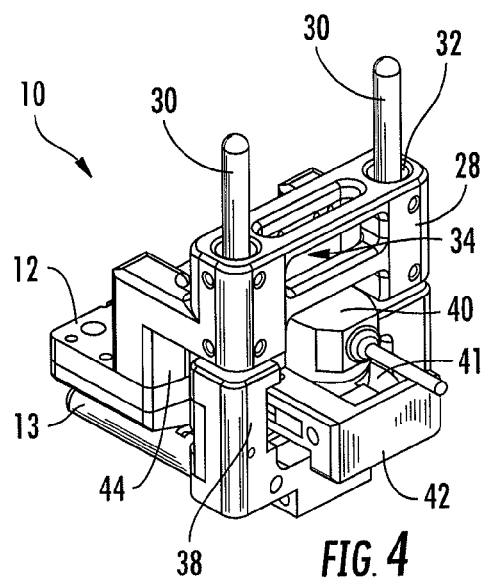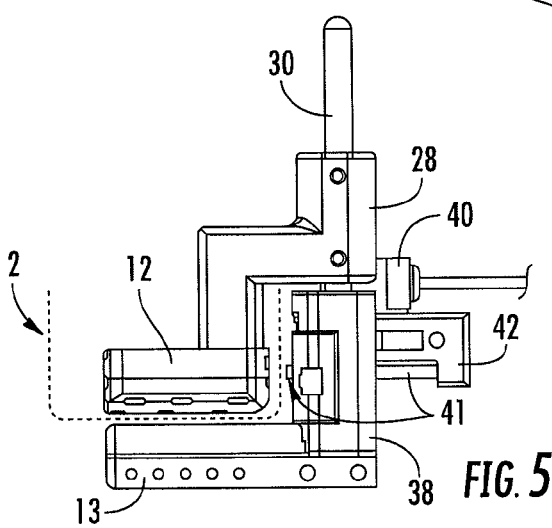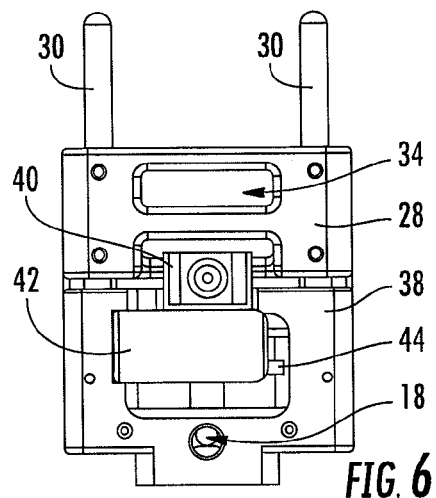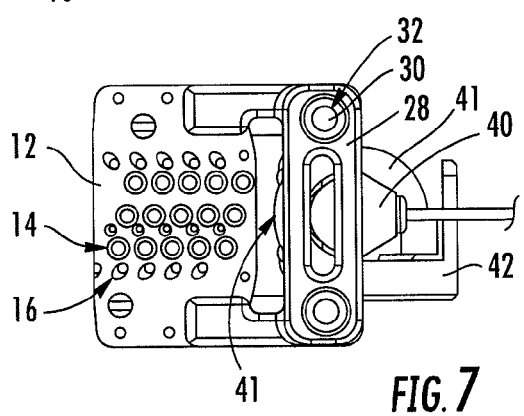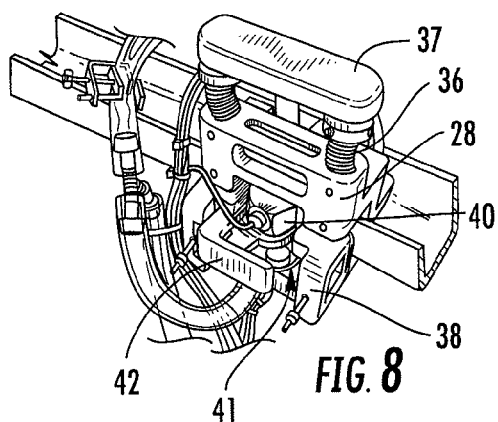

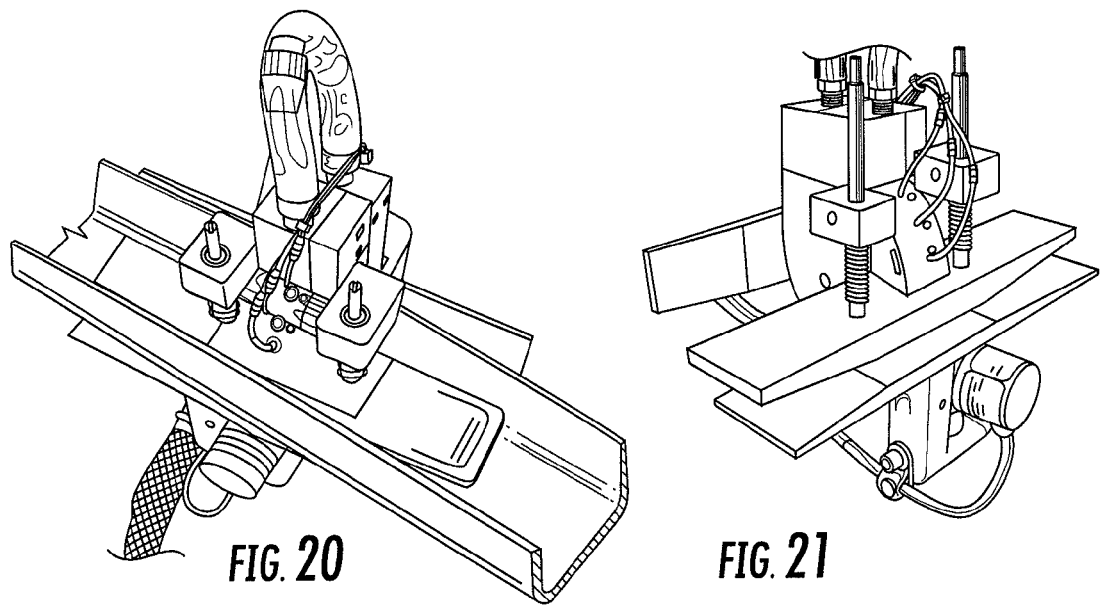
FIG. 20
FIG. 21
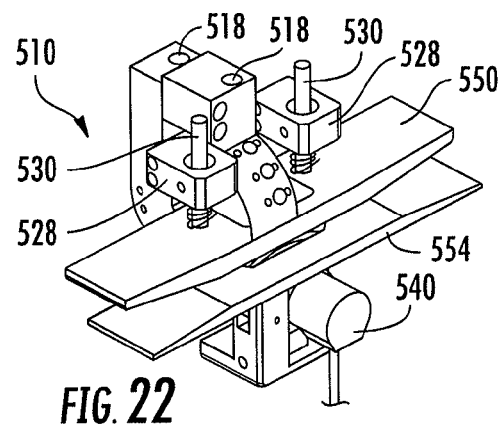
FIG. 22
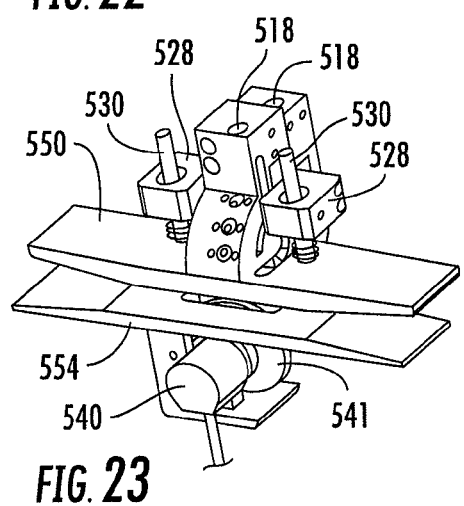
FIG. 23

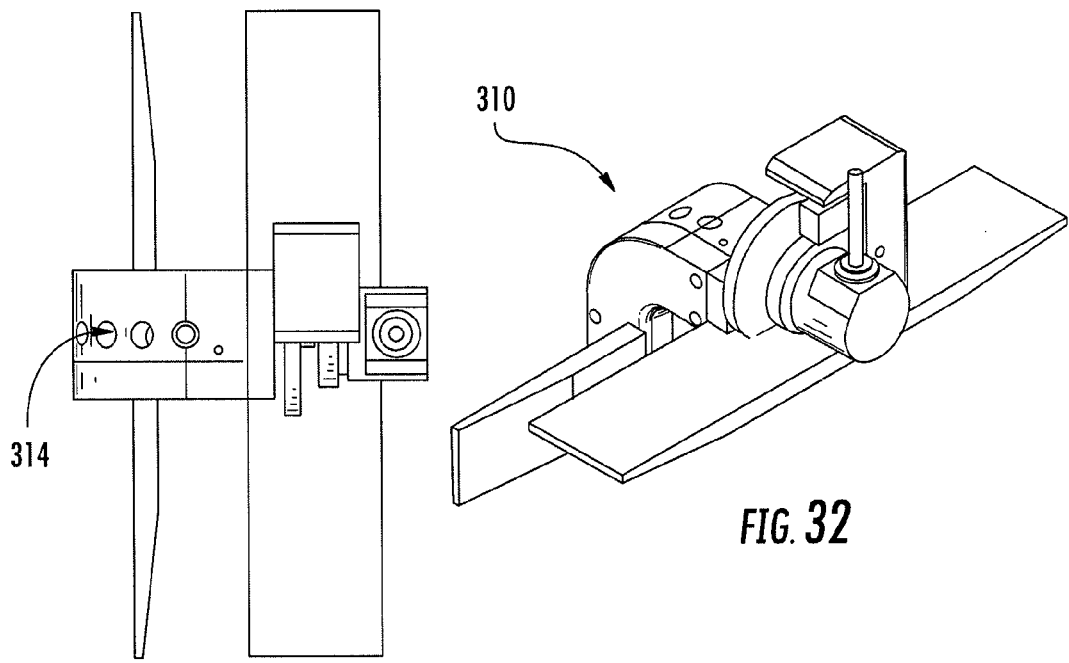
FIG. 31
FIG. 32
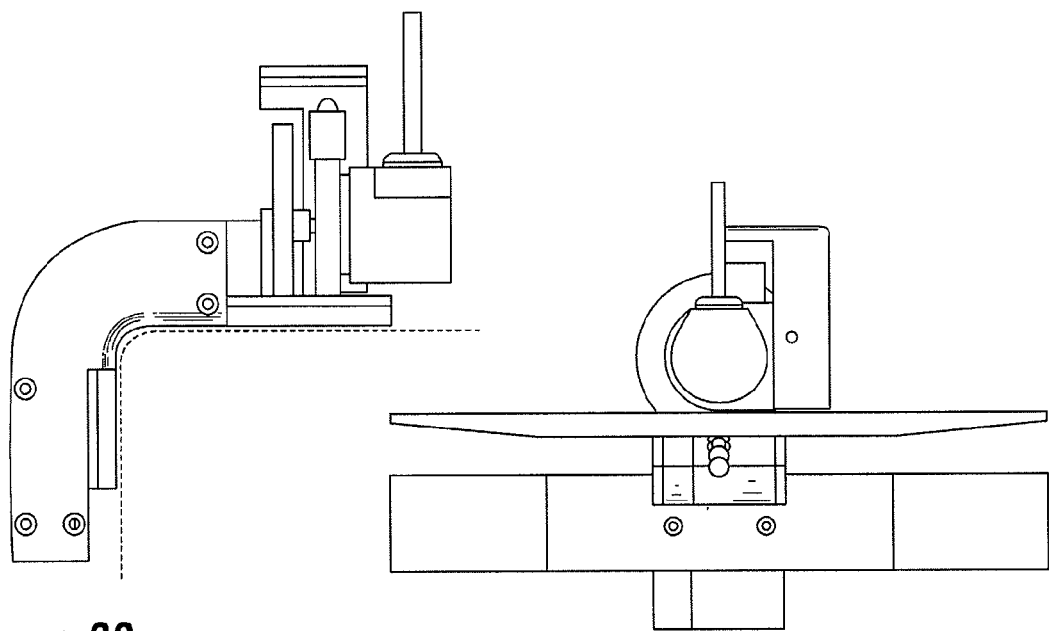
FIG. 33
FIG. 34

INTEGRATED ULTRASONIC INSPECTION PROBES, SYSTEMS, AND METHODS FOR INSPECTION OF COMPOSITE ASSEMBLIES

CROSS-REFERENCE TO RELATED APPLICATIONS

This application is a continuation of and claims priority to U.S. patent application Ser. No. 11/477,686, filed Jun. 29, 2006 now U.S. Pat. No. 7,464,596, which is a continuation-in-part of co-pending application Ser. No. 11/368,557, entitled "Integrated Curved Linear Ultrasonic Transducer Inspection Apparatus, Systems, and Methods," filed Mar. 6, 2006, which is a continuation-in-part of application Ser. No. 11/213,652, entitled "Rapid Prototype Integrated Curved Linear Ultrasonic Transducer Inspection Apparatus, Systems, and Methods," filed Aug. 26, 2005, to issue as U.S. Pat. No. 7,444,876 on Nov. 4, 2008; application Ser. No. 10/949,625, entitled "Multi-Channel Multiplexed Inspection System and Method," filed Sep. 24, 2004, now U.S. Pat. No. 7,254,519; application Ser. No. 11/178,584, entitled "Ultrasonic Inspection Apparatus, System, and Method," filed Jul. 11, 2005; and application Ser. No. 11/178,637, entitled "Ultrasonic Array Probe Apparatus, System, and Method for Traveling Over Holes and Off Edges of a Structure," filed Jul. 11, 2005, now U.S. Pat. No. 7,337,673, the contents each of which are incorporated herein by reference in their entireties.

The contents of U.S. Pat. No. 6,722,202; application Ser. No. 10/943,088, entitled "Magnetically Attracted Inspecting Apparatus and Method Using a Ball Bearing," filed Sep. 16, 2004, now U.S. Pat. No. 7,395,714; application Ser. No. 10/943,135, entitled "Magnetically Attracted Inspecting Apparatus and Method Using a Fluid Bearing," filed Sep. 16, 2004, now U.S. Pat. No. 7,320,249; and application Ser. No. 11/041,499, entitled "Non-Destructive Stringer Inspection Apparatus and Method," filed Jan. 24, 2005, now U.S. Pat. No. 7,249,512, are incorporated herein by reference in their entireties.

FIELD OF THE INVENTION

The present invention relates generally to apparatus, systems, and methods for inspecting a structure and, more particularly, embodiments of the present invention relate to apparatus, systems, and methods for non-destructive inspection of a composite assembly structure using integrated part-riding ultrasonic inspection sensors with a portable function support system.

BACKGROUND

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing of a structure or after the completed structure has been put into service, including field testing, to validate the integrity and fitness of the structure during manufacturing and ongoing and future use while in-service.

Among the structures that are routinely non-destructively tested are composite structures, such as composite sandwich structures and other adhesively bonded panels and assemblies and structures with contoured surfaces. For example, airframes may incorporate composite structures, such as hat stringers or hat stiffeners made from carbon fiber reinforced and graphite epoxy (Gr/Ep) materials and co-cured or co-bonded hat stringers and, similarly, composite fuselage frames and shear ties. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, foreign materials, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum or delamination which may occur between adjacent composite layers. However, the features and characteristics of many structures do not easily permit non-destructive inspection. For example fuselage frames and shear ties often have diameters of up to 11 feet and conventionally require large immersion tanks to facilitate inspection, along with complex support mechanisms, all of which occupy large areas at fixed locations.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo, or impedance sensors may be used to provide indications of voids or porosity, such as in adhesive bondlines of the structure. High resolution inspection of an aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive ultrasonic testing often involves coupling an ultrasonic signal from a transducer or transducer array to the surface of the structure under inspection, such as bubbling water between an inspection device and the structure. While solid laminates may be inspected using one-sided pulse echo ultrasonic (PEU) testing and bondline thickness may be measured using one-sided pulse echo ultrasonic testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display.

Non-destructive inspection may be performed manually by technicians who move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides of a structure which, at least in some circumstances, will be problematic, if not impossible, particularly for semi-automated systems that use a fixed frame for control of automated scan heads.

Automated inspection systems have also been developed as an alternative to manual and semi-automated inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. Similarly, a scanning system may include a linear or curved linear ultrasonic transducer (in comparison to an unordered or matrix array and describe further herein). However, typically each structure and inspection application requires a corresponding transducer or transducer array designed to provide transducer alignment (position and orientation with respect to the surface(s) of the structure) and scan coverage for the structure. Conventionally, special inspection devices are constructed for scanning different structures and different sizes and configurations of structures. Designing an inspection device for scanning a particular structure requires ensuring proper alignment of the inspection sensors with respect to the surface(s) of the structure and ensuring scan coverage of the structure. For example, consideration must be taken for flat and curved surfaces as well as features of the structure, including radius features such as convex edges and concave corners. Constructing specialized inspection devices for each inspection application conventionally has required significant time and financial and human resources to design and build these specialized inspection devices. Also, conventionally, each specialized inspection device is designed for and capable of only inspecting one structure, and typically cannot adjust for different sizes of the structure or different inspection applications that use different sensors. And any inspection device must ultimately overcome the difficulties of interacting with the structure being inspected and the characteristics thereof, many structures being shaped and sized to prevent easily accomplishing non-destructive inspection.

Accordingly, a need exists for improved non-destructive inspection apparatus, systems, and methods for inspecting certain structures having unique structural components.

SUMMARY OF THE INVENTION

Improved apparatus, systems, and methods are provided for inspecting structures such as fuselage frames with curved linear U-shaped cross-section structural features and fuselage shear ties with L-shaped individual flange structural features using one or more inspection sensors with a portable function support system. Embodiments of apparatus and systems of the present invention use parts, such as a sensor holder, which may typically be constructed from rapid prototyping, wherein the sensor holder is configured to support an ultrasonic inspection sensor aligned for inspection of at least a portion of a surface of a structure. Embodiments of methods of the present invention provide fast and efficient methods for inspecting structures with inspection probes designed to accommodate unusually shaped structures and a portable function support systems to facilitate inspection of the structures by the probes.

An embodiment of an apparatus of an inspection probe of the present invention may include sensor holders with sensor recesses for inspection sensors. The sensor holders may be configured for traveling over opposing surfaces of two portions of a structure under inspection, where the two portions are separated by a radius feature. An inspection probe may be designed for inspecting any of the first portion of the structure, such as a fuselage frame flange; the second portion of the structure, such as a fuselage frame web; and the radius therebetween, such as a fuselage frame radius. According to another embodiment of the present invention, an inspection probe may be designed for inspecting a fuselage shear tie using a similarly configured sensor holder for riding over the flange and web of the shear tie and orienting inspection sensors at the shear tie radius. Sensor holders of inspection probes of embodiments the present invention may include wing appendages for supporting the sensor holders on the structure. Embodiments of inspection probes may include positional encoders and fluid manifolds for improving the performance of the inspection operation.

According to another aspect of the present invention, a portable function support system may include a computer, fluid pump, controller, and software program. These components may be configured to be portable, such as by mounting the components on a moveable cart, thereby providing a portable function support system for facilitating the needs of inspection probes for performing non-destructive inspection of a part. In addition to performing data analysis, the computer may also be used to control the fluid pump, such as to turn on or off the fluid pump or to open and close flow valves of a manifold associated with the fluid pump for controlling the flow of a fluid couplant to different inspection probes.

According to yet another aspect of the present invention, a computer program includes control logic code for selecting predefined structures and/or predefined inspection probes for performing different inspection operations. Additional control logic code may perform real-time analysis and visual display of inspection data. Further, control logic code may be included to coordinate inspection data with control logic to coordinate inspection data from one or more of the different inspection probes, thereby providing a coordinated visual representation of the inspection data in a form representative of the structure under inspection.

These and other characteristics, as well as additional details, of the present invention are further described in the Detailed Description with reference to these and other embodiments.

BRIEF DESCRIPTION OF THE DRAWINGS

Figure 1:
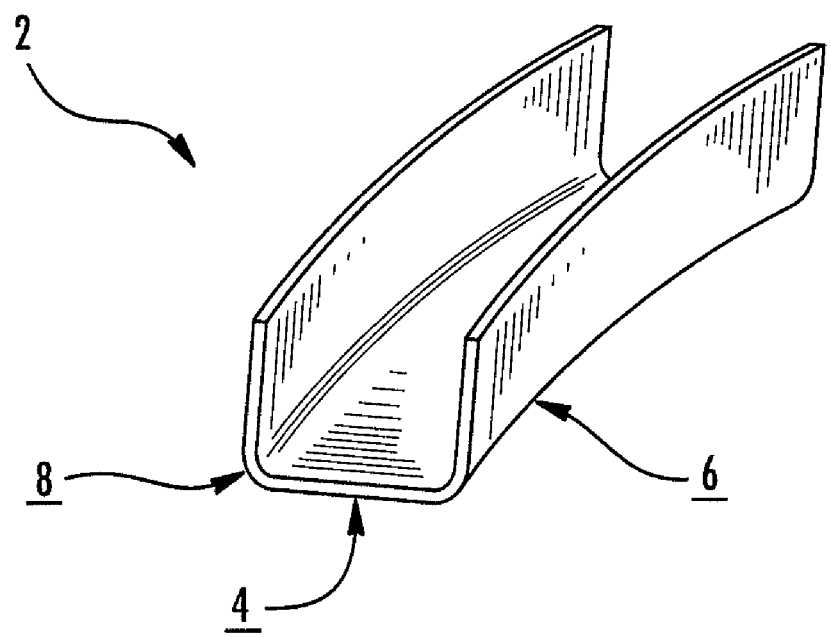
Figure 2:
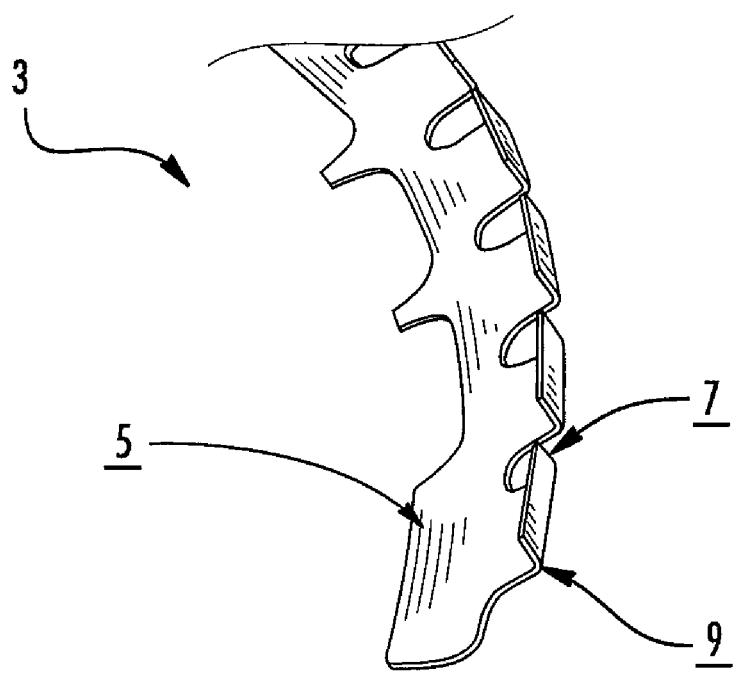
Figure 9:
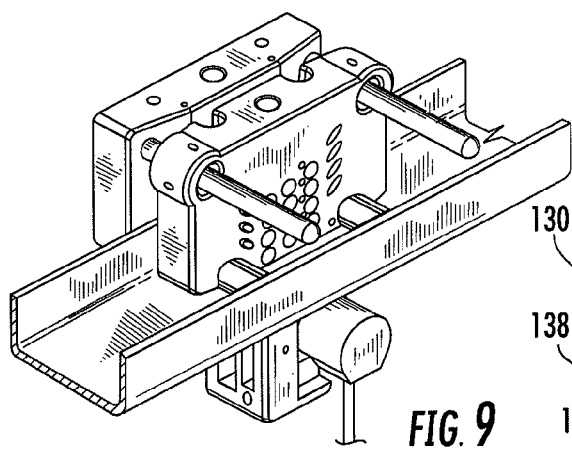
Figure 10:
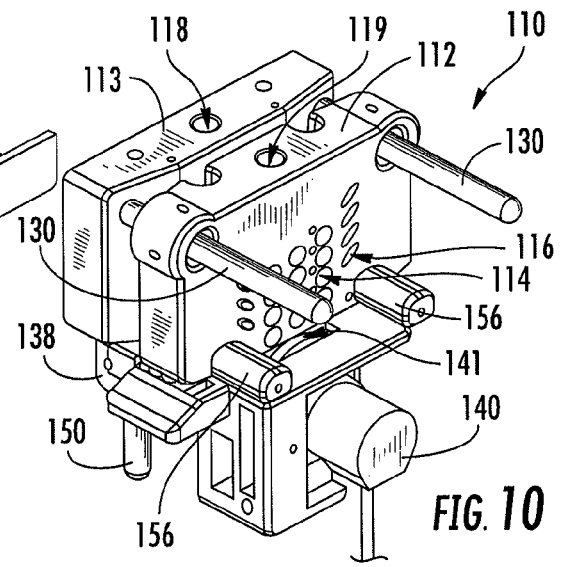
Figure 11:
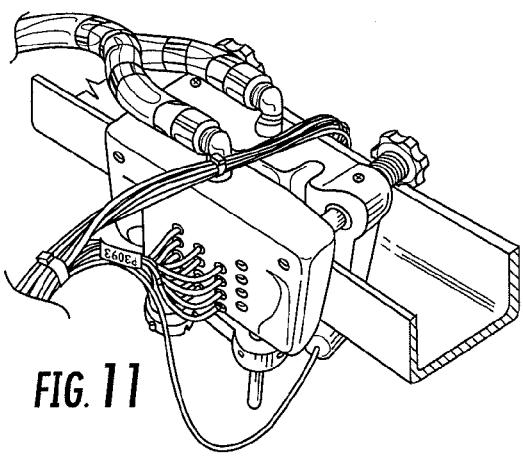
Figure 12:
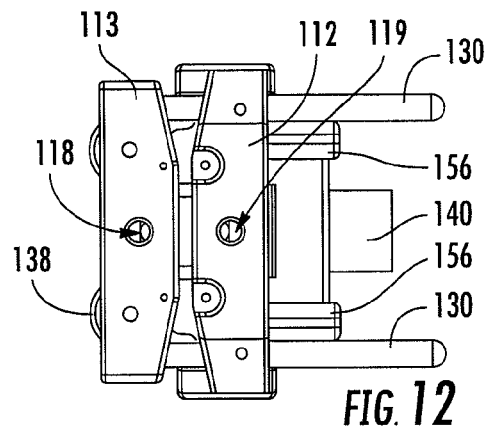
Figure 13:
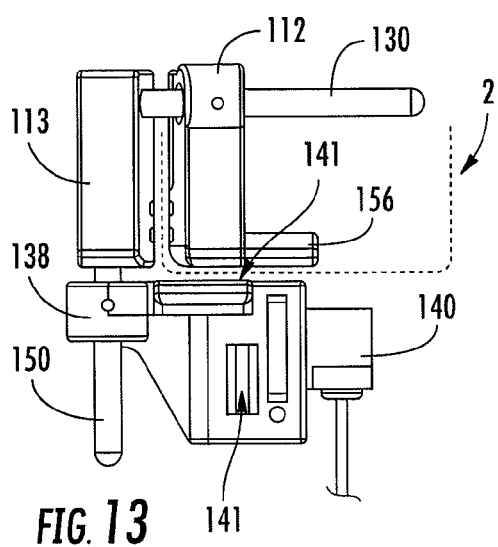
Figure 14:
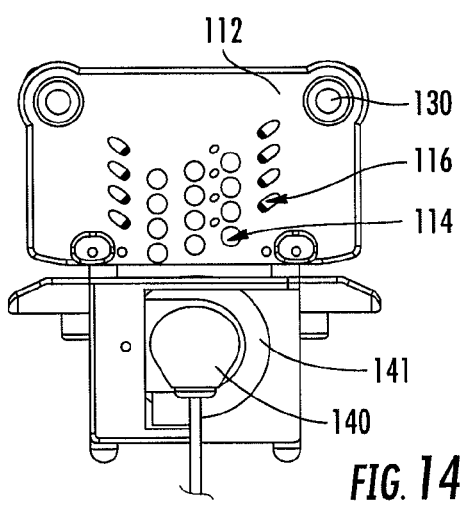
Figure 15:
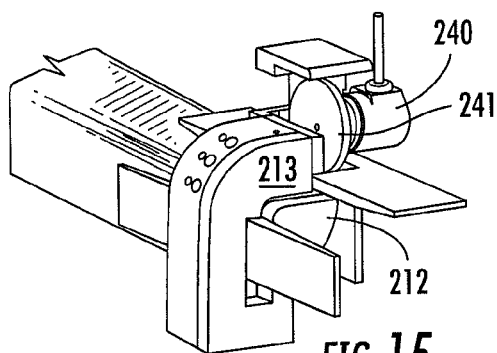
Figure 16:
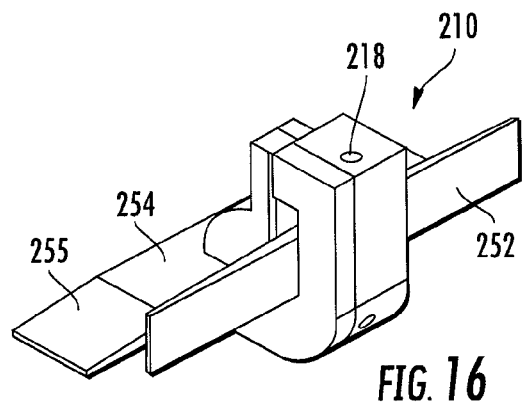
Figure 17:
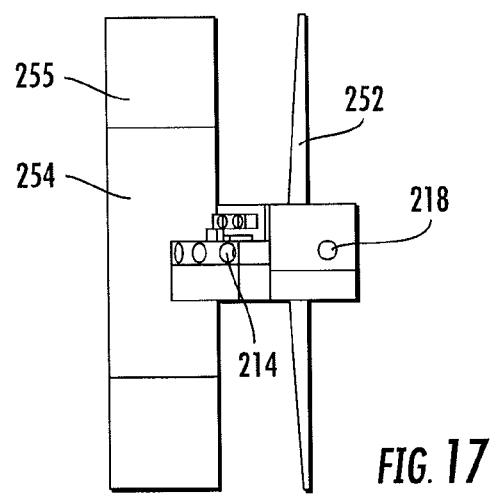
Figure 18:
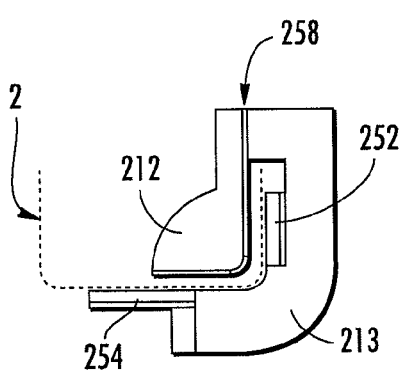
Figure 19:
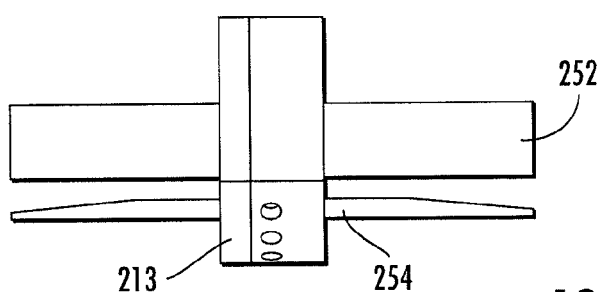
Figure 24:
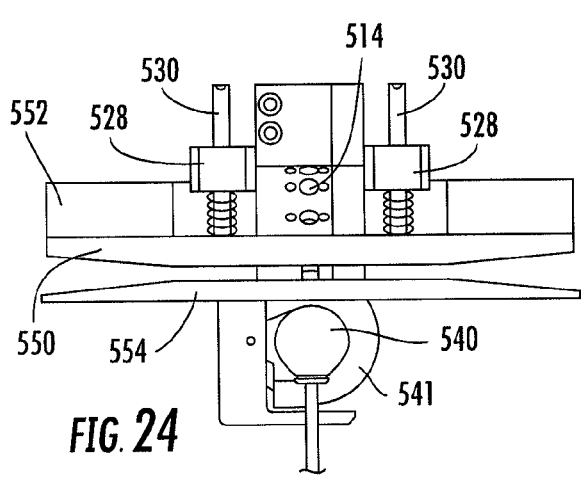
Figure 25:
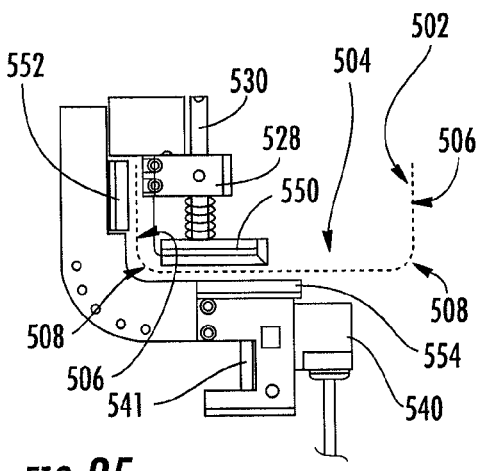
Figure 26:
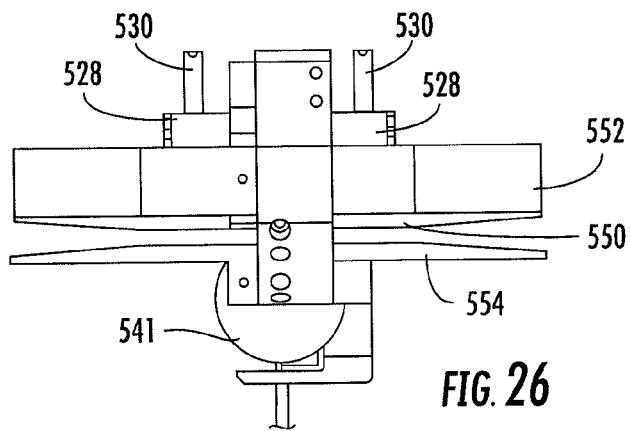
Figure 27:
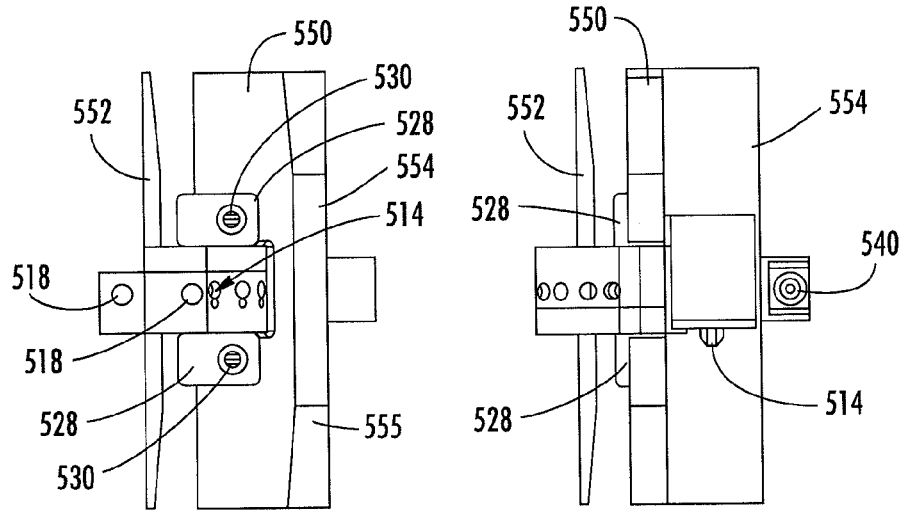
Figure 28:
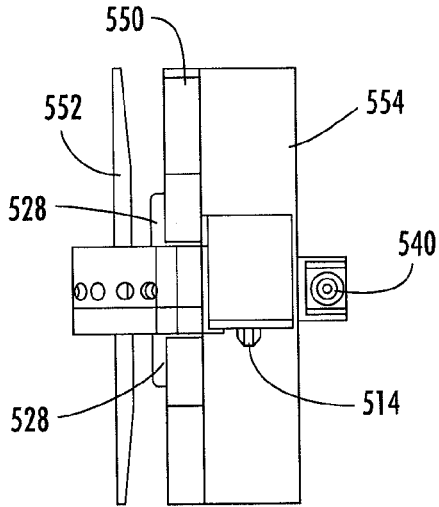
Figure 29:
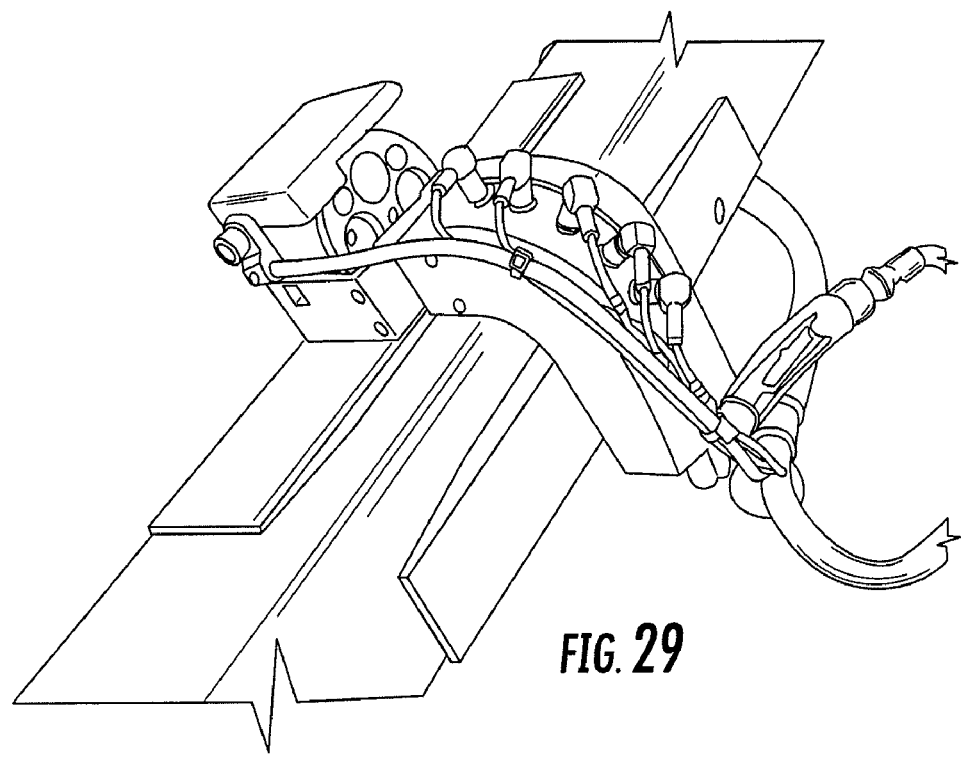
Figure 30:
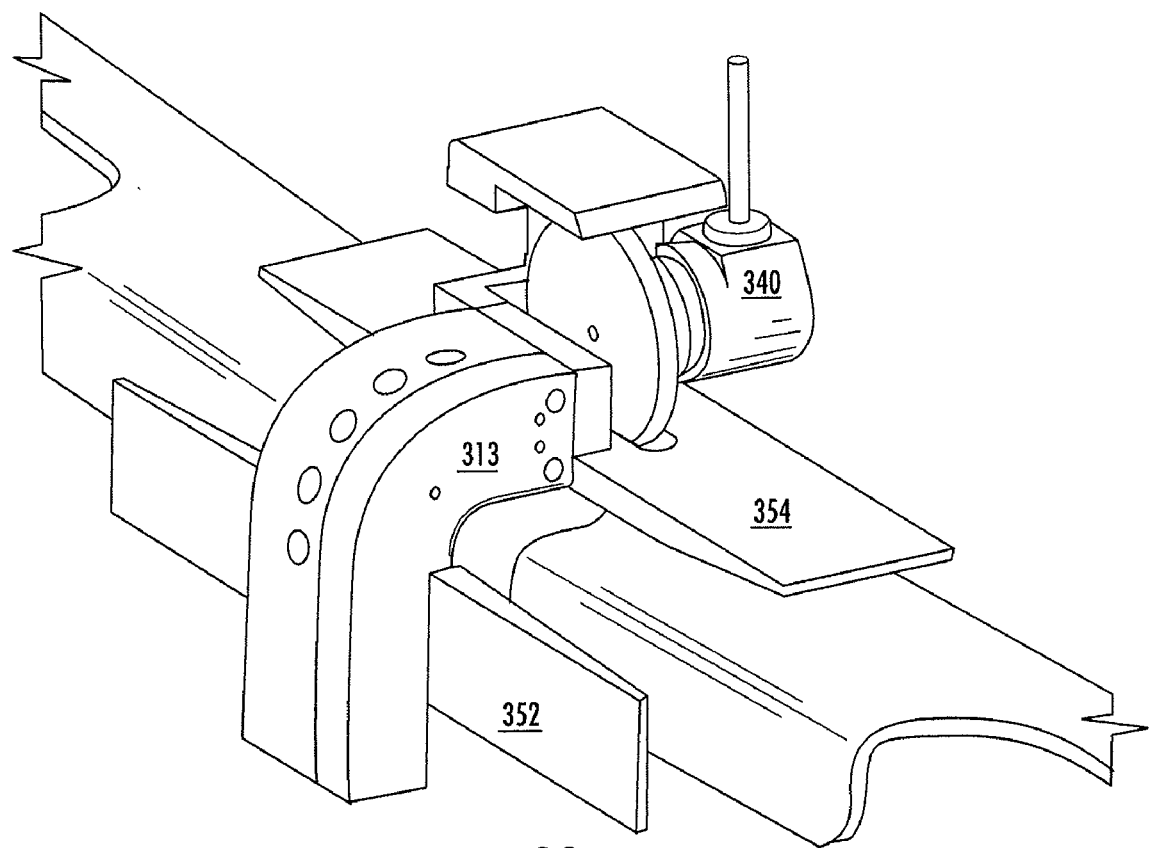
Figure 35:
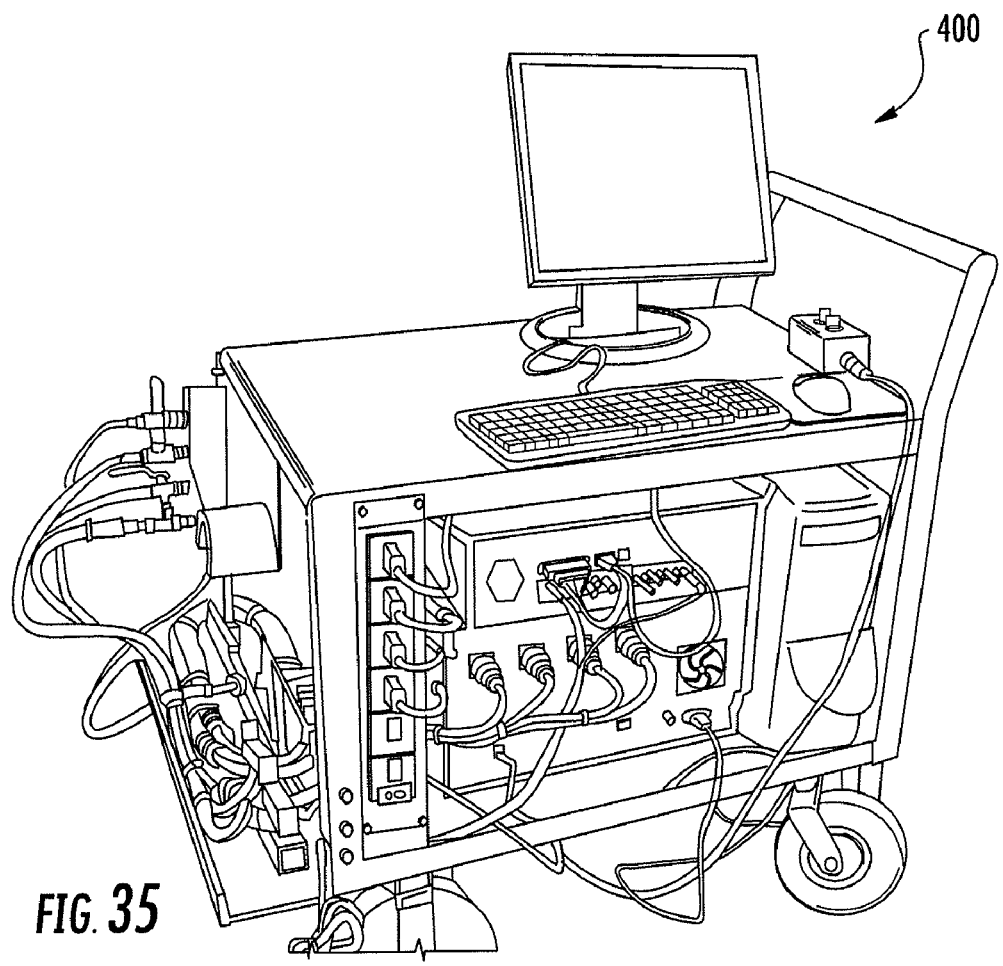
Figure 36:
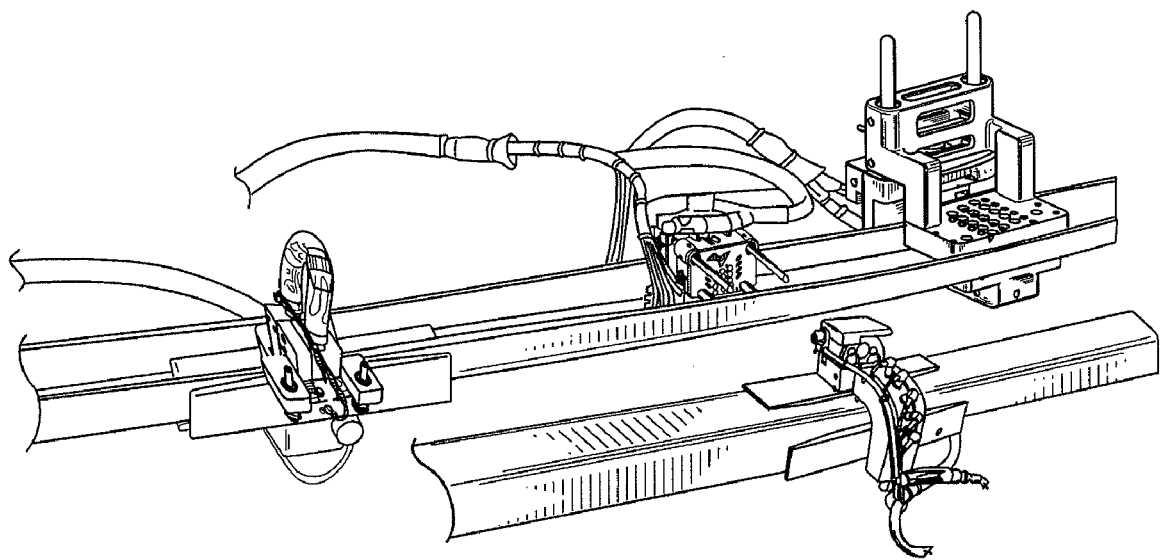
Figure 37:
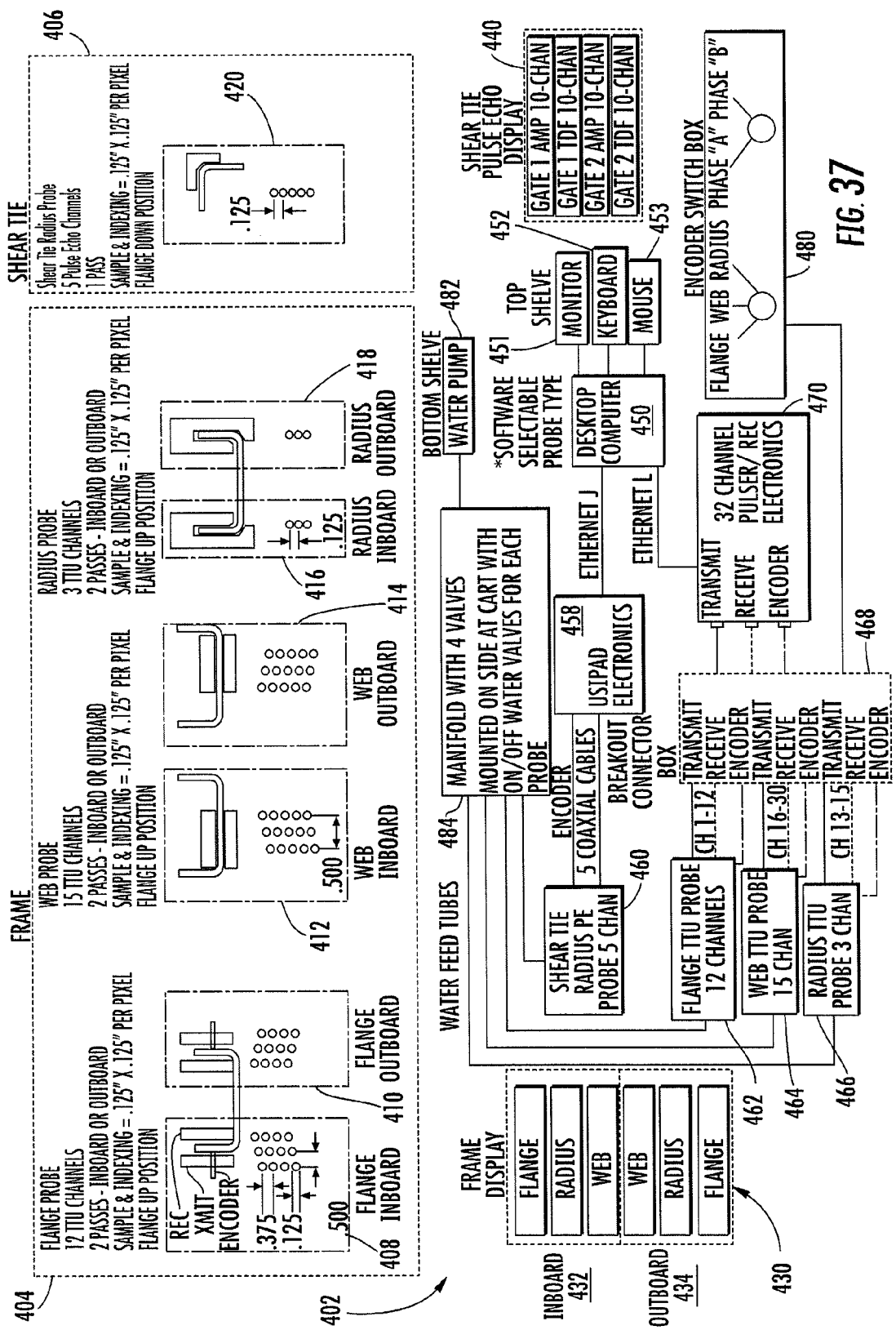
Figure 38:
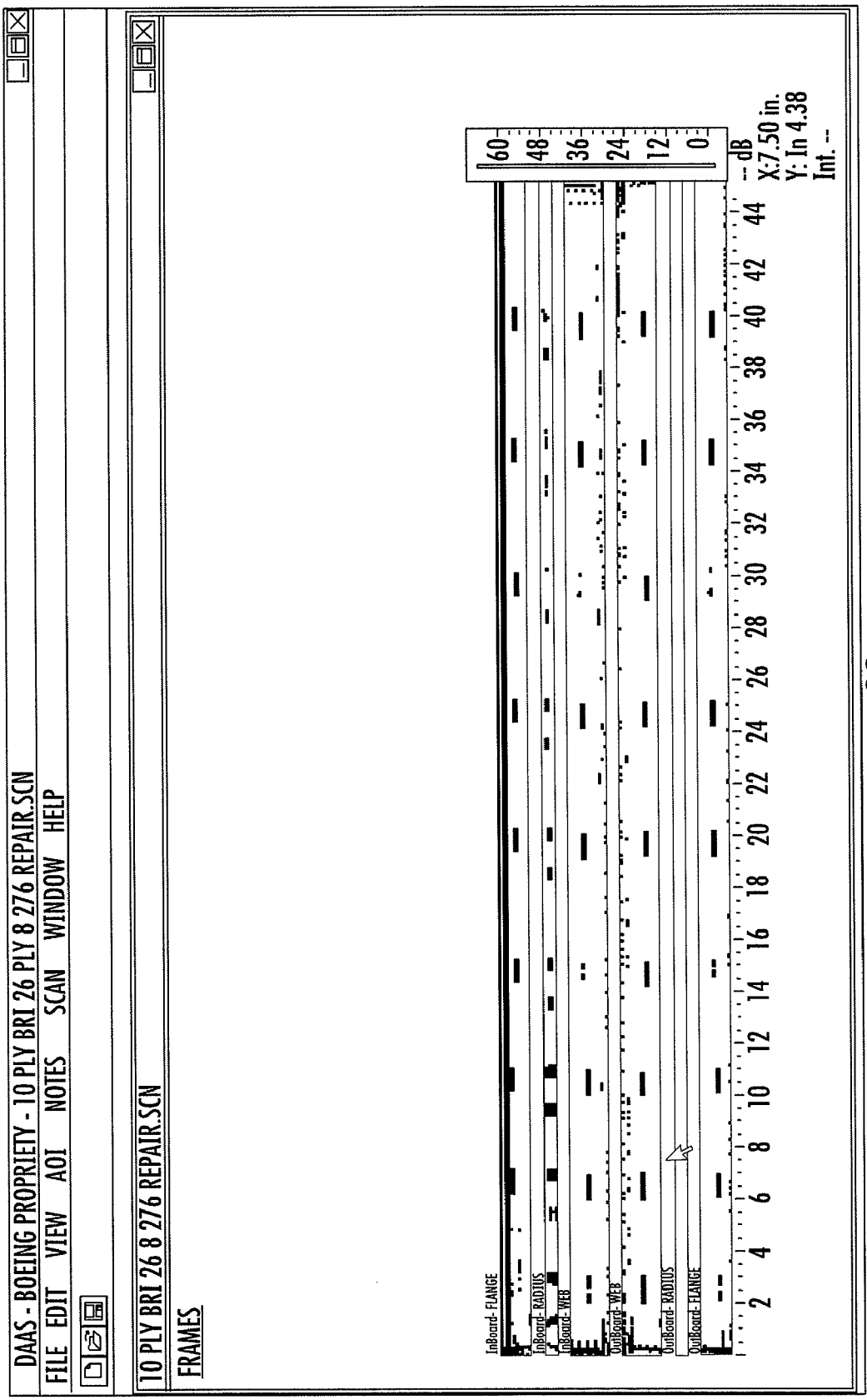
Figure 39:
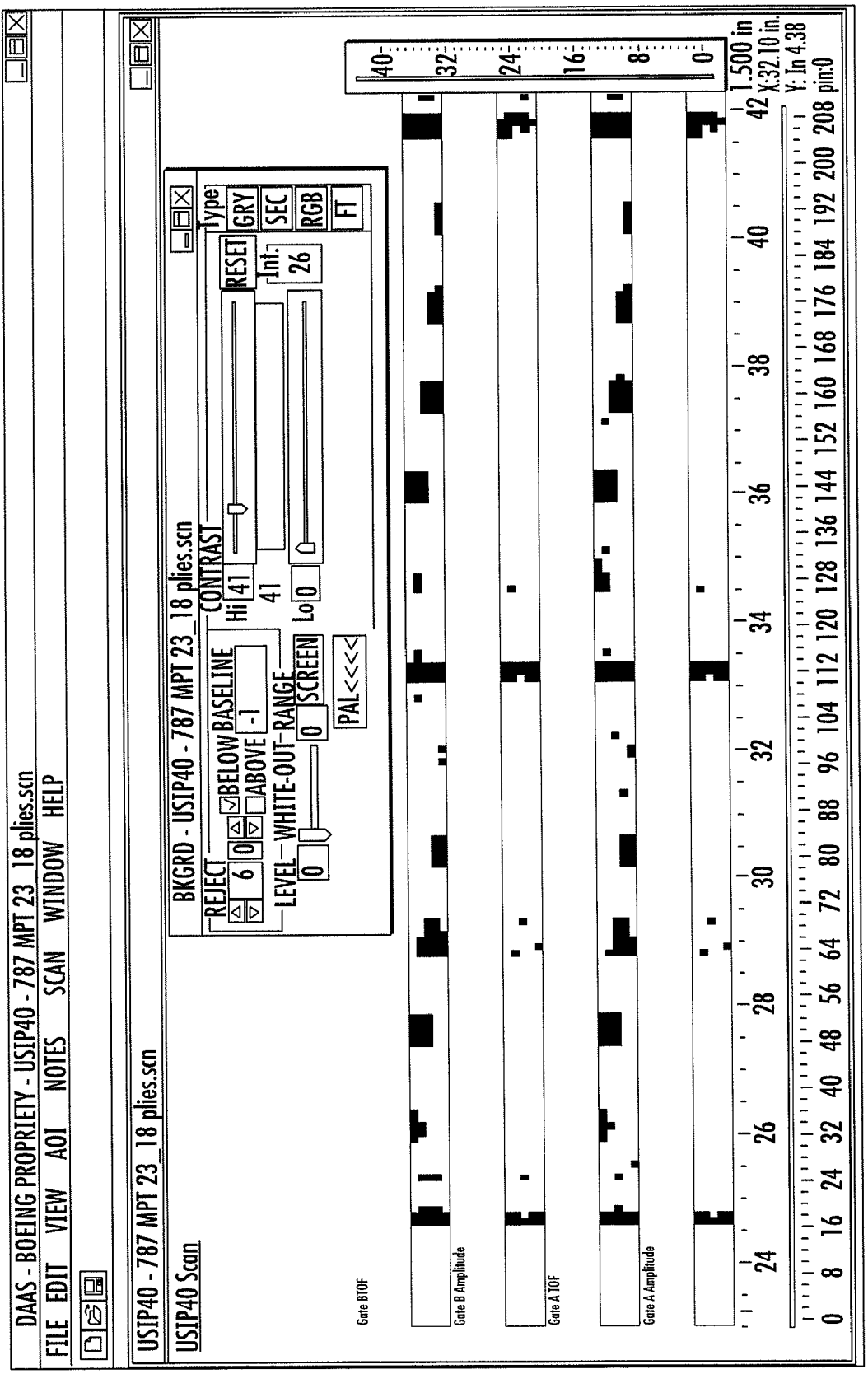
Figure 40:
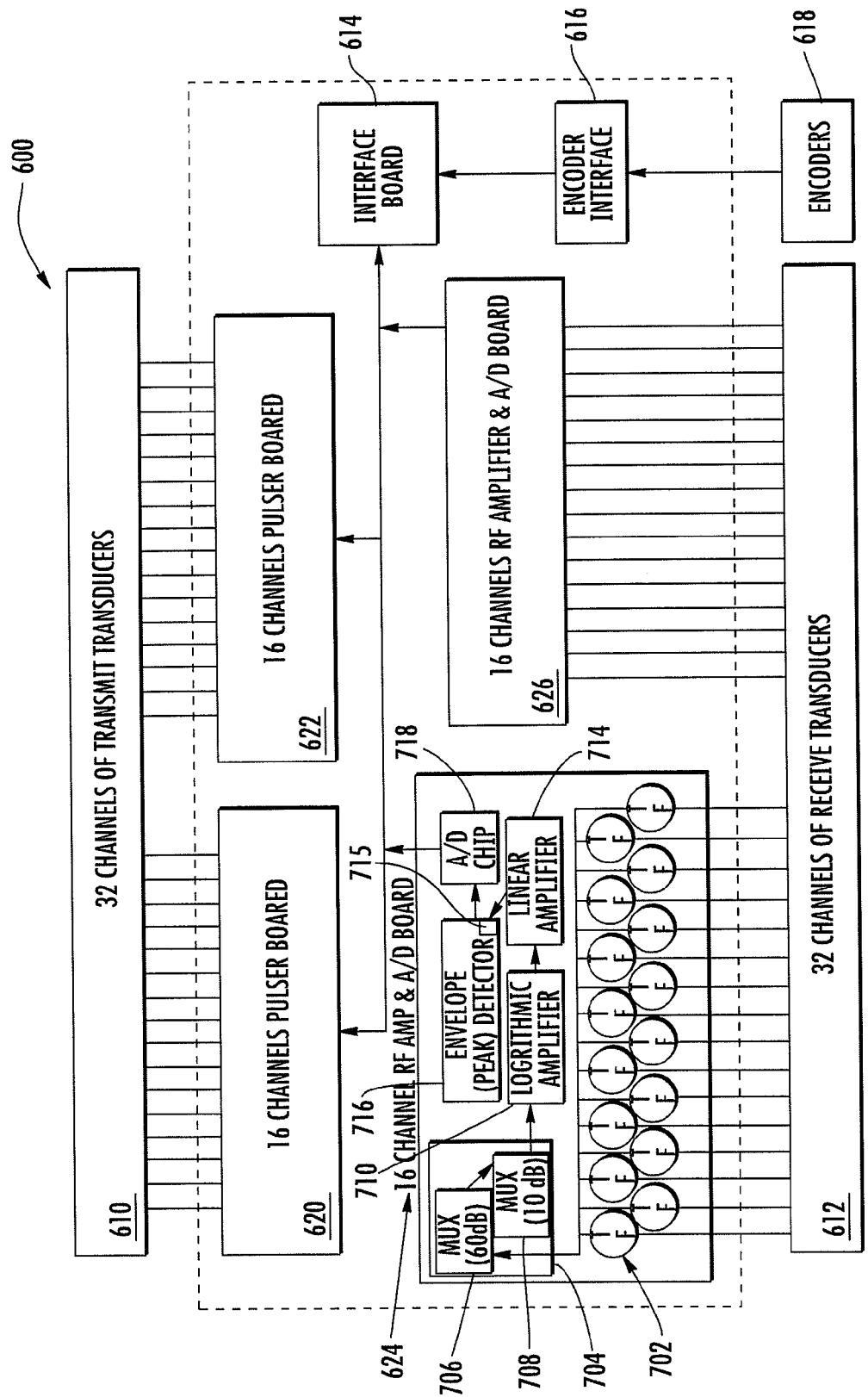
Figure 41:
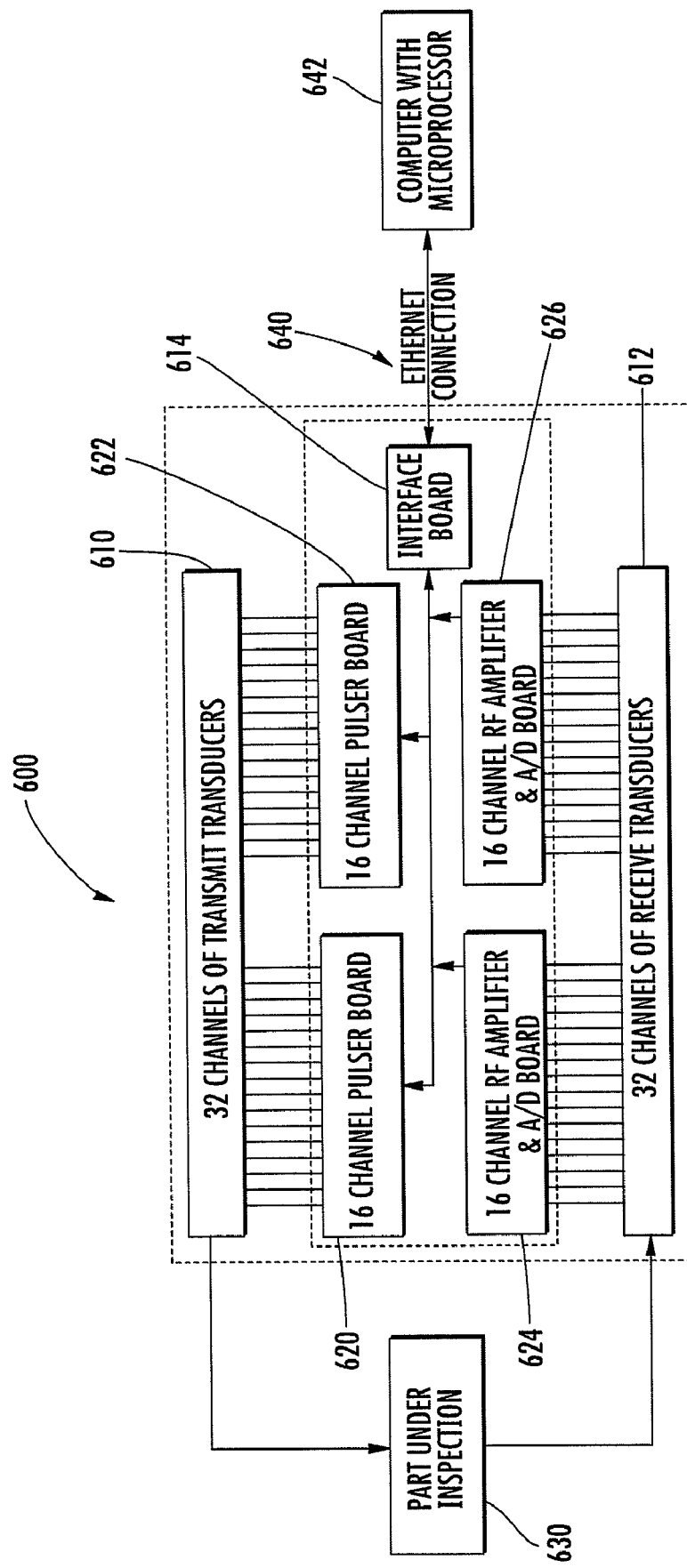

Having thus described the invention in general terms, reference will now be made to the accompanying drawings, which are not necessarily drawn to scale, and wherein:

FIG. 1 is a perspective view of a cross-section and portion of a fuselage frame;

FIG. 2 is a perspective view of a cross-section and portion of a fuselage shear tie;

FIG. 3 is a perspective view of a fuselage frame inspection device of an embodiment of the present invention for inspecting flanges of fuselage frames;

FIG. 4 is another perspective view of the inspection device of FIG. 3;

FIG. 5 is a side elevation plan view of the inspection device of FIG. 3;

FIG. 6 is a front elevation plan view of the inspection device of FIG. 3;

FIG. 7 is a bottom plan view of the inspection device of FIG. 3;

FIG. 8 is yet another a perspective view of inspection device of FIG. 3 shown in operation with a spring-loaded force mechanism, data wiring connected to ultrasonic transducers and a positional rotary encoder, and fluid flow tubing;

FIG. 9 is a perspective view of a fuselage frame inspection device of an embodiment of the present invention for inspecting webs of fuselage frames;

FIG. 10 is another perspective view of the inspection device of FIG. 9;

FIG. 11 is yet another perspective view of the inspection device of FIG. 9 shown in operation with a spring-loaded force mechanism, data wiring connected to ultrasonic transducers and a positional rotary encoder, and fluid flow tubing;

FIG. 12 is a top plan view of the inspection device of FIG. 9;

FIG. 13 is a side elevation plan view of the inspection device of FIG. 9;

FIG. 14 is a front elevation plan view of the inspection device of FIG. 9;

FIG. 15 is a perspective view of a fuselage frame inspection device of an embodiment of the present invention for inspecting radii between webs and flanges of fuselage frames;

FIG. 16 is another perspective view of the inspection device of FIG. 15;

FIG. 17 is a top plan view of the inspection device of FIG. 15;

FIG. 18 is a side elevation plan view of the inspection device of FIG. 15;

FIG. 19 is a front elevation plan view of the inspection device of FIG. 15;

FIG. 20 is a perspective view of another fuselage frame inspection device of an embodiment of the present invention for inspecting radii between webs and flanges of fuselage frames shown in operation with data wiring connected to ultrasonic transducers and a positional rotary encoder and fluid flow tubing;

FIG. 21 is another perspective view of the inspection device of FIG. 20;

FIG. 22 is yet another perspective view of the inspection device of FIG. 20;

FIG. 23 is yet another perspective view of the inspection device of FIG. 20;

FIG. 24 is a rear elevation plan view of the inspection device of FIG. 20;

FIG. 25 is a side elevation plan view of the inspection device of FIG. 20;

FIG. 26 is a front elevation plan view of the inspection device of FIG. 20;

FIG. 27 is a top plan view of the inspection device of FIG. 20;

FIG. 28 is a bottom plan view of the inspection device of FIG. 20;

FIG. 29 is a perspective view of a fuselage shear tie inspection device of a embodiment of the present invention shown in operation with data wiring connected to ultrasonic transducers and a positional rotary encoder and fluid flow tubing;

FIG. 30 is another perspective view of the inspection device of FIG. 29;

FIG. 31 is a top plan view of the inspection device of FIG. 29;

FIG. 32 is yet another perspective view of the inspection device of FIG. 29;

FIG. 33 is a side elevation plan view of the inspection device of FIG. 29;

FIG. 34 is a front elevation plan view of the inspection device of FIG. 29;

FIG. 35 is a perspective view of a portable function support system for non-destructive inspection of a structure;

FIG. 36 is a perspective view of multiple probes for use with the portable function support system of FIG. 35;

FIG. 37 is a diagram of the portable function support system of FIG. 35;

FIG. 38 is a graphical user interface display for operating with the portable function support system of FIG. 35 to perform fuselage frame inspection;

FIG. 39 is another graphical user interface display for operating with the portable function support system of FIG. 35 to perform fuselage shear tie inspection;

FIG. 40 is a schematic block diagram of a multi-channel multiplexed through transmission ultrasonic inspection system; and FIG. 41 is a schematic block diagram of a multi-channel multiplexed through transmission ultrasonic inspection system connected to a remote processor using an Ethernet connection.

DETAILED DESCRIPTION

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

While embodiments of the present invention are shown and described herein with reference to through transmission ultrasonic (TTU) and pulse echo ultrasonic (PEU) non-destructive inspection using individual inspection sensors (i.e., individual transducer transmitters, receivers, and transceivers), embodiments of the present invention are not limited to use of individual inspection sensors, but may be implemented using linear or curved linear inspection sensors, i.e., inspection sensors having preconfigured ordered or matrix transducer arrangements. For example, a linear transducer could be oriented with the width of a fuselage frame flange or fuselage frame web normal to the linear direction of the scanning operation to inspect a surface area the size of the length of the linear transducer by the length of travel of the inspection device.

A linear inspection sensor, also referred to as a linear array, linear array inspection sensor, or linear transducer, refers to an inspection sensor including a plurality of transducers, typically spaced and arranged at equal distances, which are oriented in a straight line, or offset in more than one line, to inspect over a planar length, rather than at a point. A linear inspection sensor transmits inspection signals in parallel through a plane. Using a linear inspection sensor is advantageous for inspecting a flat surface area of a structure, particularly when inspection occurs by translating an inspection probe over a flat or gradually curved length of surface of the structure under inspection.

Similarly, a curved linear inspection sensor may be used for inspection of a radius feature of a structure. A curved linear inspection sensor, also referred to as a curved linear array, curved linear array inspection sensor, or curved linear transducer, refers to an inspection sensor including a plurality of transducers, typically spaced and arranged at equal distances, which are oriented in either a convex or concave curved shape, such as in a convex shape to inspect a concave curved radius feature or in a concave shape to inspect a convex curved radius feature. The terms curved shape and curved radius feature are used herein to refer to shapes and features which are characteristic of either being smoothly and continuously curved/arcuate or having any other concave or convex shape that is not smoothly and continuously curved, such as a compound curve or linear sections joining at angles. A curved linear array transmits inspection signals at angles through a plane, either diverging if convex or converging if concave. Using a curved linear inspection sensor may be advantageous for inspecting curved radius features of structures, rather than inspecting such curved features using individual point inspection sensors or linear inspection sensors transmitting inspection signals in parallel through a plane, even where two linear inspection sensors or two passes of one linear inspection sensor overlap to cover the curved radius feature. A curve linear inspection sensor is better suited to inspect curved radius features than a linear inspection sensor.

Embodiments of integrated ultrasonic inspection probes, systems, and methods of the present invention are described herein with respect to inspection of fuselage frames and shear ties. However, the apparatus, systems, and methods of the present invention may also be used for structures other than fuselage frames and shear ties and similar applications which require non-destructive inspection, including without limitation other composite structures with difficult-to-inspect geometric configurations and/or remote locations, particularly those with U-shaped and L-shaped cross-sections. Embodiments of apparatus, systems, and methods of the present invention may be used for manual hand scanning by a technician or using a semi-automatic or automatic motion control system. Further, as an alternative to an application of a physical constant force, such as a spring-loaded force, for supporting an inspection probe on opposing sides of a structure for TTU inspection, apparatus, systems, and methods may possibly also using magnetic coupling such as described with reference to the magnetically coupled probes in co-pending application Ser. Nos. 10/943,088; 10/943,135; and 11/041, 499.

Further, embodiments of the present invention are described with reference to the manufacturing and/or production using rapid prototyping. Rapid prototyping involves slicing an electronic design model into electronic layers which are physically built up to create the end product, such as stereolithography which constructs three-dimensional end products from liquid photosensitive polymers (e.g., liquid epoxy or acrylate resin) that solidify when exposed to ultraviolet light (e.g., low-power focused UV laser that traces out each layer). Stereolithography is further described in U.S. Pat. No. 4,575,330 to Hull, assigned to 3D Systems, Inc., of Valencia, Calif. Other types of rapid prototyping are also possible, such as laminated object manufacturing, selective laser sintering, fused deposition modeling, solid ground curing, silicon molding and urethane casting, high density nylon membranes, machining Delrin, and 3-D ink-jet printing. Rapid prototyping does not require tooling because the end product is produced directly from an electronic design model, typically a CAD model. Because rapid prototyping does not require tooling, it provides a relatively inexpensive and fast method of manufacturing a custom inspection device. Rapid prototyping is particularly advantageous for custom inspection devices because a CAD model can be created for the particular application corresponding to the structure to be inspected, and a corresponding inspection device can be created. Embodiments of the present invention can be created in relatively little time, for relatively low cost while still being designed specifically for a particular inspection application, even if the structure to be inspected has a unique shape or surface contour. Rapid prototyping permits creation of inspection devices with custom shapes for custom inspection applications according to the corresponding shapes and features of the structure to be inspected, such as the curved edges and multi-sided surfaces of fuselage frames and shear ties. Accordingly, embodiments of apparatus and systems according to the invention may be designed and constructed to accommodate variations of structure shapes, sizes, and other characteristics, such as different fuselage frame and shear tie design shapes, sizes, and part thickness changes.

FIG. 1 is a perspective view of a cross-section and portion of a fuselage frame. The portion of the fuselage frame 2 is shown having a U-shaped cross-section with vertical flange walls 6, individually referred to as a flange, each flange having parallel sides linearly but being formed of a curved surface. The flanges 6 of the frame 2 are separated by a web 4 which is formed of a planar surface with curving sides linearly. Each flange 6 is connected to the web 4 through a radius 8.

FIG. 2 is a perspective view of a cross-section and portion of a fuselage shear tie. The portion of the fuselage shear tie 3 is shown having an L-shaped cross-section with a web 5 having a planar surface in a curved shape and individual flanges 7 connected to the web 5 through individual radii 9.

FIGS. 3-8 show a first embodiment of a probe of the present invention designed for TTU inspection of the web portion of a fuselage frame. Accordingly, FIG. 3 is a perspective view of a fuselage frame inspection device of an embodiment of the present invention for inspecting flanges of fuselage frames; FIG. 4 is another perspective view of the inspection device of FIG. 3; FIG. 5 is a side plan view of the inspection device of FIG. 3; FIG. 6 is a front plan view of the inspection device of FIG. 3; FIG. 7 is a bottom plan view of the inspection device of FIG. 3; and FIG. 8 is yet another a perspective view of inspection device of FIG. 3 shown in operation with a spring-loaded force mechanism, data wiring connected to ultrasonic transducers and a positional rotary encoder, and fluid flow tubing. The cumulative collection of figures showing this inspection probe are discussed herein together below and specific reference to a particular figure is merely a convenient reference for visual identification in such figure and not a distinction from any other figure for the inspection probe except were specifically noted, such as with respect to the spring-loaded force mechanism, data wiring connected to ultrasonic transducers and a positional rotary encoder, and fluid flow tubing of FIG. 8.

The inspection probe of FIG. 3 is designed with surface-sides (the portions of the apparatus proximate and/or riding on a structure under inspection) of the sensor holders corresponding to the shape of at least a portion of the surface of the structure. A structure of an inspection apparatus for supporting an ultrasonic inspection sensor is referred to herein as a sensor holder, regardless of the manner of fabrication, such as whether fabricated by a rapid prototyping technique or by alternate method. The inspection probe of FIG. 3 is designed for inspecting a fuselage frame web and, thus, has sensor holders with parallel planar surface sides for contacting and riding along opposing surfaces of the web. The inspection probe is further designed (shaped, sized, etc.) to conform to the structure, such as to fit within the width of the web between the flanges of the frame and to travel over and around one flange of the frame. To do so, the inspection probe includes an L-shaped recess to accommodate a portion of the web and a flange, as visible in FIG. 5.

The design and use of the sensor holders permits full inspection coverage of a portion of the web of the fuselage flange. Because the probe is designed for TTU inspection, a first sensor holder 12 is designed to be positioned between the flanges and within the U-shaped recess above a surface of the web. A second sensor holder 13 is designed to be positioned on the opposite surface of the web from the first sensor holder 12. Accordingly the two sensor holders operate in coordination with each other to support and orient transducers therein which correspond to perform transmit and receive operations for TTU inspection. Transducers are supported and oriented in the sensor holders in transducer recesses 14. Corresponding diagonal openings 16 may be provided in the sensor holders to accommodate set screws for ensuring transducers do not move within transducer recesses.

Inspection devices, and particularly the sensor holders of inspection devices, of embodiments of the present invention are designed to correspond to the shape and size of structures to be inspected. Inspection probe which are designed for TTU inspection generally may be referred to as a clam shoe (i.e., probe or shoe with clam-like appearance) due to the probe closing around a structure to support sensor holders on opposing surfaces of the structure. For example, the inspection device 10 of FIG. 3 includes two parallel rods 30 to act as guides to direct the clam shoe closure of the inspection probe around the fuselage frame and upon the web thereof and to ensure parallel alignment of the sensor holders on opposing sides of the web. Springs 36 or other constant force means, such as a pneumatic piston or the like, may be used to force the first sensor holder 12 onto the web and thereby pull the second sensor holder 13 up against the opposing surface of the web. When using a spring-loaded force to close the clam-like operation of the inspection probe 10, a support cap 37 may be affixed to the top of the rods 30 to provide a surface against which the springs may press to force against the upper portion 28 of the inspection probe 10. Alignment of the sensor holders is achieved, in part, by the linear nature of the first sensor holder 12 sliding along cylindrical openings 32 in an upper portion 28 of the inspection probe which accommodate linear movement of the upper portion along the rods. The constant application of force, such as from the spring-loaded rods, ensures the sensor holders contact and ride along the web for traveling over and inspecting at least a portion of the web of the fuselage frame. The rods are fixed with respect to the second sensor holder 13 by being rigidly disposed within at least a portion of a lower portion 38 of the inspection probe 10.

To compensate for surface variations of the structure, such as shape and contour characteristics of a surface or imperfections in a surface, surface-sides of an inspection probe, i.e., those portions of the apparatus proximate and/or riding on a structure under inspection, such as sensor holders, generally may be tapered at outer portions of the inspection probe, as the tapered surfaces 44 which are partially visible in FIGS. 3 and 4, and like tapered surfaces more clearly visible, for example, in FIGS. 9-14 with respect to an embodiment of a fuselage flange inspection probe of the present invention.

To assist in manual scanning operations and handling the inspection probe, a handle or handle opening 34 may be provided in a portion of the inspection probe, such as in a conveniently accessible portion of the inspection probe, such as the upper portion 28.

For ultrasonic inspection operations, a fluid, such as water or air, can be fed through one or more supply lines through a fluid inlet port and into one or more recesses, such as defined channels or manifolds, a central cavity, or similar openings that permit the flow of fluid through the inspection probe and/or sensor holder(s) thereof (generally referred to herein as a "fluid manifold" characteristic structural feature of an inspection probe). A fluid manifold for an inspection probe is the structure of one or more internal water passages to feed the transducers in a sensor holder. The particular design of a fluid manifold is intended to disperse a fluid between the inspection probe and a surface of the structure under inspection, particularly between the inspection sensors supported by sensor holders of the inspection probe and a surface of the structure, thereby coupling ultrasonic signals between the inspection sensors and the structure. This process is known as fluid coupling. Generally an attempt is made to have the fluid flow smoothly between the inspection sensors and the structure without bubbles, cavitations, or turbulence that might detrimentally affect the signal to noise ratio of the ultrasonic inspection signals. The inspection probe 10 includes a fluid inlet port 18 to which fluid supply lines may be connected to deliver a fluid couplant to the inspection device 10. The fluid inlet port 18 would be connected to internal fluid manifolds within the sensor holder 13 that are configured to pass the fluid couplant from the fluid inlet port 18 to the area between the inspection sensors held by the second sensor holder 13 and the structure under inspection, specifically, a surface of the web of the fuselage frame. A similar fluid inlet port and fluid manifold may be provided to couple inspection sensors of the first sensor holder 12. A fluid manifold may be formed of any number of shapes and merely represents a defined passage from a fluid inlet port to an area through which ultrasonic inspection signals pass for controlling the flow of fluid from the fluid inlet port to the area through which ultrasonic inspection signals pass.

Because contact with a surface of a structure may be interrupted, such as where a probe is located over a hole or partially off an edge of a structure, a special fluid manifold may be used with a sensor holder, i.e., a bubbler shoe. A bubbler shoe disperses a couplant around each ultrasonic transducer to independently couple the signal from each transducer to the surface of the structure under inspection, rather than using a single cavity to couple all of the transducers. Bubbler shoes are described further, for example, in application Ser. No. 11/178,637. By individually coupling each transducer to the surface of the part, the bubbler shoe compensates for when a portion of the probe travels over a hole or off an edge of the structure. In such a manner, only the transducers over the hole or off the edge of the structure will lose the coupling with the surface, but the transducers remaining over the surface of the structure will continue to be independently coupled.

Contact with the surface of a structure under inspection ensures consistent orientation of transducers with respect to the structure for ultrasonic inspection. Contact with the surface also permits accurate position measurement of the inspection device during continuous scanning by keeping a positional encoder in physical and/or visual contact with the surface of the structure under inspection. The inspection probe 10 also includes an encoder 40 with a wheel 41, such as an optical shaft encoder (OSE), rotational encoder, optical encoder, or linear encoder, for recording motion or position information of the inspection probe 10 with respect to the fuselage frame 2 being inspected. Although encoders are typically used to provide position information, encoders may additionally or alternatively be used to provide such data as speed data, velocity data, and distance data. The encoder 40 and wheel 41 are mounted to an encoder carrier portion 42 of the inspection probe. Regardless of the particular structural mounting for an encoder, it may be advantageous to provide a physical application of constant force, such as from a spring-loaded bias, to press the encoder against the structure to ensure constant contact between the encoder, or wheel thereof, and the structure and thereby ensure the encoder operates to record the inspection probe traveling along the structure. As such, by using the application of a constant force, contact between the encoder and structure need not merely be provided by gravity.

Similarly to the use of a wheel attachment for an encoder, other embodiments of inspection devices in accordance with the present invention may be used with a drive motor or like automated drive mechanism to semi-automatically or automatically move an inspection device along a structure for inspection; alternatively, a magnetically coupled crawler or motion controlled robotic arm maybe use may be used to control movement of an inspection device along a structure for inspection.

FIGS. 9-14 show a second embodiment of a probe of the present invention designed for TTU inspection of the flange portion of a fuselage frame. Accordingly, FIG. 9 is a perspective view of a fuselage frame inspection device of an embodiment of the present invention for inspecting webs of fuselage frames; FIG. 10 is another perspective view of the inspection device of FIG. 9; FIG. 11 is yet another perspective view of the inspection device of FIG. 9 shown in operation with a spring-loaded force mechanism, data wiring connected to ultrasonic transducers and a positional rotary encoder, and fluid flow tubing; FIG. 12 is a top plan view of the inspection device of FIG. 9; FIG. 13 is a side plan view of the inspection device of FIG. 9; and FIG. 14 is a front plan view of the inspection device of FIG. 9. The cumulative collection of figures showing this inspection probe are discussed herein together below and specific reference to a particular figure is merely a convenient reference for visual identification in such figure and not a distinction from any other figure for the inspection probe except were specifically noted, such as with respect to the spring-loaded force mechanism, data wiring connected to ultrasonic transducers and a positional rotary encoder, and fluid flow tubing of FIG. 11.

The inspection probe 110 of FIG. 9 is much like the inspection probe 10 of FIG. 3, but having orientation of components such that the clam-like operation of the inspection probe closes down on a fuselage flange for inspection thereof with corresponding inspection sensors therefore. Like the inspection probe 10 of FIG. 3, the inspection probe 110 of FIG. 9 defines an L-shaped opening into which a fuselage flange and portion of a fuselage web pass, as depicted in FIG. 13. The inspection probe 110 also includes two rods 130 to support and align the movement of a first sensor holder 112 with respect to a second sensor holder 112. Similarly, the inspection probe 110 of FIG. 9 includes transducer recesses 114 for supporting and orienting transducers in the first sensor holder 112 and the second sensor holder 112 for TTU inspection of the flange. Further, like the inspection probe 10 of FIG. 3, the inspection probe 110 of FIG. 9 includes fluid inlet ports 118, 119 for coupling a fluid between inspection sensors in the sensor holders and the fuselage flange. However, unlike the inspection probe 10 of FIG. 3 which includes a spring-loaded encoder mounted to an encoder carrier, inspection probe 110 of FIG. 9 includes two additional rods 150 to support movement of a lower portion 138 of the inspection probe with respect to the position of the second sensor holder 113. By way of the configuration of these components of the inspection probe 110 of FIG. 9, the inspection probe is designed to clamp down on both the flange and the web of the fuselage frame, and the clamping of the lower portion 138 provides a contact between the wheel 141 of the encoder 140 and a surface of the web of the fuselage frame. To aid in maintaining stable position across the width of the web, the inspection probe 110 includes two support extensions 156 which increase the width of the first sensor holder 112 across a portion of the web. These extra support extensions 156 help stabilize the support of the inspection probe 110 across the web.

FIGS. 15-19 show a third embodiment of a probe of the present invention designed for TTU inspection of the radius portion of a fuselage frame. Accordingly, FIG. 15 is a perspective view of a fuselage frame inspection device of an embodiment of the present invention for inspecting radii between webs and flanges of fuselage frames; FIG. 16 is another perspective view of the inspection device of FIG. 15; FIG. 17 is a top plan view of the inspection device of FIG. 15; FIG. 18 is a side plan view of the inspection device of FIG. 15; and FIG. 19 is a front plan view of the inspection device of FIG. 15. The cumulative collection of figures showing this inspection probe are discussed herein together below and specific reference to a particular figure is merely a convenient reference for visual identification in such figure and not a distinction from any other figure for the inspection probe except were specifically noted.

While the inspection probe of FIG. 15 is still designed to perform TTU inspection of a structure, the probe is designed with a rigid, fixed shape and orientation for the first sensor holder 212 and second sensor holder 213, thereby ensuring constant separation and orientation of radially directed inspection sensors in corresponding radially directed transducer recesses 214. Probes operating TTU inspections require constant separation between transmitting and receiving transducers, having fixed relative positions and distances. Accordingly, while a flange or web probe may be able to rely upon a consistent thickness of the flange or web to maintain constant separation, a radius probe may need to be constructed in a fixed position due to changes in the thickness of the radius, such as from accurate tooling on the outer convex radius and lack of accurate tooling on the inner convex radius or changes in thickness due to frame repairs to a radius which may add as much as a quarter inch to the thickness of the radius. Accordingly, the inspection probe 210 of FIG. 15 is shown with a fixed separation between the transmit transducers and receive transducers mounted to a first sensor holder 212 positioned inside the concave curve of the radius and a second sensor holder 213 positioned outside the convex curve of the frame radius. To permit the inspection probe 210 to surround a flange and portion of the web of a fuselage frame, the inspection probe 210 may be designed to separate for installation and removal, such as at location 258 between the first sensor holder 212 and second sensor holder 213.

Of particular importance with respect to the inspection probe 210 of FIG. 15 is the orientation of inspection sensors in radially directed transducer recesses 214. This orientation provides the inspection probe 210 the ability to perform TTU inspection operations providing coverage for the radius portion of a fuselage flange.

As with the inspection probes 10, 110 of FIGS. 3 and 9, the inspection probe 210 of FIG. 15 also includes transducer recesses 214, a positional encoder 240 with a wheel 241 for riding along a surface of the part under inspection, and fluid inlet ports 218. Because the inspection probe 210 does not include a clam-like configuration to ensure consistent support against the structure, wing appendages 252, 254 are affixed to the second sensor holder 213 so as to place the wing appendages 252, 254 with surface-side orientations with respect to an outer surface of a flange and outer surface of the web of a fuselage frame. Wing appendages, also referred to as wings, are linear extensions attached to the probe and upon which the probe rides over a surface of the structure. Wing appendages may also be transverse (width) extensions to provide both linear and transverse support for the probe to travel over a surface of the structure. Wing appendages may be used to compensate for surface variations of the structure, such as shape or contour characteristics of a surface. Wing appendages generally have tapered ends on the surface of the wing appendages which will be adjacent to a surface of a structure to account for any changes or variations in the surface of the structure over which the probe rides.

Although not shown in the figures hereof, an inspection probe may also include contact members as described and depicted more fully in application Ser. Nos. 11/368,557 and 11/213,652 to extend outwardly from the face or surface of the sensor holder of the inspection device that faces respective surfaces of a structure under inspection. More particularly, surface-side portions of an inspection probe, such as sensor holders and wing appendages, including tapered surfaces thereof, may include contact members. Various types of contact members can be used, such as roller bearings, ball bearings, needle bearings, fluid bearings, skids or the like. Skids may include a Teflon® material available from E.I. DuPont Nemours and Company of Wilmington, Del., on a surface of the skid for contact with the surface of the structure being inspected and to provide for translation thereacross. Skids may be beneficial to prevent damage or marring of a surface of a structure under test when initially placing an inspection device on a structure. Roller, ball, needle, an other types of low-friction bearings may be beneficial for providing ease of motion of the inspection device over the surface of the structure being inspected. Fluid bearings, such as water bearings and air bearings, may be used to maintain spacing and orientation of an inspection device with respect to a structure under inspection. Bearings, skids, and the like may be used to reduce the fiction between the inspection device and the surface of the structure under inspection, such as displace the probe from contacting the surface of the structure using hydraulic flotation or a hydrostatic bearing. Use of contact members may provide smooth translation of an inspection device over the surface of a structure to allow an inspection device to maintain an intended direction, maintain alignment of inspection sensors, and allow continuous scanning of a surface regardless of size, smoothness, or flatness of the surface, such as to permit easy rolling of the inspection device. Further, use of a skid or fluid bearing between the inspection device and the surface of the structure may prevent scratching of soft skins or denting of panels of the skins.

FIGS. 20-28 show another fuselage frame inspection device of an embodiment of the present invention. By comparison to the inspection probe of FIG. 15, which is designed with a rigid, fixed shape and orientation for the first sensor holder 212 and second sensor holder 213, thereby ensuring constant separation and orientation of radially directed inspection sensors in corresponding radially directed transducer recesses 214, the inspection probe of FIG. 20 includes a spring-loaded wing 550 to provide for clam-like operation and hold the inspection probe 510 at a constant, rigid position in height with respect to the fuselage frame web 504. FIG. 20 is a perspective view of another fuselage frame inspection device of an embodiment of the present invention for inspecting radii between webs and flanges of fuselage frames shown in operation with data wiring connected to ultrasonic transducers and a positional rotary encoder and fluid flow tubing. FIG. 21 is another perspective view of the inspection device of FIG. 20. FIG. 22 is yet another perspective view of the inspection device of FIG. 20. FIG. 23 is yet another perspective view of the inspection device of FIG. 20. FIG. 24 is a rear elevation plan view of the inspection device of FIG. 20. FIG. 25 is a side elevation plan view of the inspection device of FIG. 20. FIG. 26 is a front elevation plan view of the inspection device of FIG. 20. FIG. 27 is a top plan view of the inspection device of FIG. 20. FIG. 28 is a bottom plan view of the inspection device of FIG. 20.

The probe 510 includes rods 530 affixed to the spring-loaded wing 550 and which guide the spring-loaded wing 550 with respect to a pair of corresponding upper portion guides 528. As visible in FIG. 25, the spring-loaded wing 550 permits the probe 510 to act with a clam-like closure to support the probe 510 by closing the spring-loaded wing 550 and a corresponding wing 554 upon opposing surfaces of a portion of the fuselage frame web 504 and by the probe 510 thereby surrounding one of the fuselage frame flanges 506 and the radius 508 therebetween. As with the inspection probes 10, 110, 210 of FIGS. 3, 9, and 15, the inspection probe 510 of FIG. 20 also includes transducer recesses 514, a positional encoder 540 with a wheel 541 for riding along a surface of the part under inspection, and fluid inlet ports 518.

FIGS. 29-34 show a fifth embodiment of a probe of the present invention designed for PEU inspection of the radius portion of a fuselage shear tie. Accordingly, FIG. 29 is a perspective view of a fuselage shear tie inspection device of a embodiment of the present invention shown in operation with data wiring connected to ultrasonic transducers and a positional rotary encoder and fluid flow tubing; FIG. 30 is another perspective view of the inspection device of FIG. 29; FIG. 31 is a top plan view of the inspection device of FIG. 29; FIG. 32 is yet another perspective view of the inspection device of FIG. 29; FIG. 33 is a side plan view of the inspection device of FIG. 29; and FIG. 34 is a front plan view of the inspection device of FIG. 29. The cumulative collection of figures showing this inspection probe are discussed herein together below and specific reference to a particular figure is merely a convenient reference for visual identification in such figure and not a distinction from any other figure for the inspection probe except were specifically noted, such as with respect to the spring-loaded force mechanism, data wiring connected to ultrasonic transducers and a positional rotary encoder, and fluid flow tubing of FIG. 29.

While the inspection probe 210 of FIG. 15 which is also designed to inspect a radius feature of a structure, the inspection probe 310 of FIG. 29 is designed to perform PEU inspection, rather than TTU inspection. As such, the inspection probe 310 only includes a first sensor holder 313 with radially directed transducer recesses 314 for PEU inspection sensors. For PEU inspections, an inspection probe may operate using, for example, a General Electric USIP40 10 channel pulser/receiver. FIG. 39 is an example of USIP40 pulse echo C-scan data.

As with the inspection probe 210 of FIG. 15 which uses wing appendages 252, 254 to support the inspection probe 210 for riding across the surface of the fuselage frame, inspection probe 310 of FIG. 29 similarly includes wing appendages 352, 354 for supporting the inspection probe 210 for riding across the surface of the fuselage shear tie. These wing appendages 352, 354, and tapered design thereof, are particularly important for movement of the inspection probe 310 over the shear tie which is discontinuous over both the web and flange portions to define individual radius and flange pairings along the length of the web. By using wing appendages, an inspection probe is capable of traversing discontinuous sections where the probe is supported on adjacent portions of the structure to the discontinuous sections by the wing appendages.

Although individual inspection probes have been described herein above for performing inspections of individual features of a structure, one or more probes may be combined, attached, or modified in accordance with the present invention to create a multi-function probe, such as where a flange probe is outfitted with transducers for inspecting both the flange and web portions of a fuselage frame member. Such combination or modification may be advantageous for accomplishing increased inspection coverage over a structure under inspection through a reduced number of passes by an inspection probe.

Because of the portable design of the above-described inspection probes which may be used in various inspection environments and locations, a portable function support system is used to provide the resources and electronic control for the inspection probes. FIG. 35 is a perspective view of a portable function support system 400 for non-destructive inspection of a structure, and FIG. 36 shows a perspective view of multiple probes for use with the portable function support system 400 of FIG. 35. By supplementing inspection probes with a portable function support system, embodiments of the present invention achieve near-limitless portability to quickly and efficiently perform non-destructive inspection operations of various structures in any location without otherwise requiring a specialized facility or machinery for the inspection to occur. To clearly understand the manner of interaction between the inspection probes and portable function support system of the present invention, it should be noted that a portable function support system is capable of operating with more than one inspection probe, independently or simultaneously.

FIG. 37 is a diagram 402 of the portable function support system of FIG. 35. This diagram is also useful as a graphical user interface and/or display for the system to help a user and/or operator to understand the features, functions, and performance of the inspection probes and portable function support system. The diagram 402 shows orientations of inspection probes and transducer configurations for embodiments of the present invention. For example, inspection probes, and configurations and features therefore, are shown in a Frame window 404. Embodiments of fuselage frame inspection probes are shown and described in the Frame window 404.

At the left of the Frame window 404, a flange probe is described as using twelve TTU channels and requiring two inspection passes, one inboard and one outboard, to complete the inspection of both flanges of a frame. The description also provides that sampling and indexing of the inspection occurs at 0.125 inch×0.125 inch per pixel of imaging data resolution. A diagram for each inspection pass is also provided for a flange inboard pass 412 and a flange outboard pass 414. Orientation with respect to being inboard and outboard is merely a referential description with respect to the inner concave curvature of a structure as inboard and the outer convex curvature of a structure as outboard. Each diagram for an inspection pass depicts the orientation of sensor holders and encoder of the inspection probe and the transducer recesses for the transmitting and receiving inspection sensors. Also noted in the diagrams of the transducer recesses for the transmitting and receiving inspection sensors are the 0.375 inch vertical separation, 0.5 horizontal column separation, and 0.125 inch row offset for the transducer recesses.

At the center of the Frame window 404, a web probe is described as using fifteen TTU channels and also requiring two inspection passes, one inboard and one outboard, to complete the inspection of the web. The description also provides that sampling and indexing of the inspection occurs at 0.125 inch×0.125 inch per pixel of imaging data resolution. A diagram for each inspection pass is also provided for a web inboard pass 416 and a web outboard pass 418. Each diagram for an inspection pass depicts the orientation of sensor holders of the inspection probe and the transducer recesses for the transmitting and receiving inspection sensors. Also noted in the diagrams of the transducer recesses for the transmitting and receiving inspection sensors are the 0.375 inch vertical separation, 0.5 horizontal column separation, and 0.125 inch row offset for the transducer recesses.

At the right of the Frame window 404, a radius probe is described as using three TTU channels and also requiring two inspection passes, one inboard and one outboard, to complete the inspection of both radii of a frame. The description also provides that sampling and indexing of the inspection occurs at 0.01 inch×0.125 inch per pixel of imaging data resolution. A diagram for each inspection pass is also provided for a radius inboard pass 408 and a radius outboard pass 410. Each diagram for an inspection pass depicts the orientation of sensor holder(s) of the inspection probe and the transducer recesses for the transmitting and receiving inspection sensors. Also noted in the diagrams of the transducer recesses for the transmitting and receiving inspection sensors is the 0.125 inch vertical separation for the transducer recesses.

Similarly, inspection probes, and configurations and features therefore, are shown in a Shear Tie window 406 which depicts a shear tie radius probe using five PEU channels and requiring only a single inspection pass. The description also provides that sampling and indexing of the inspection occurs at 0.1 inch×0.125 inch per pixel of imaging data resolution. A diagram for the PEU shear tie radius probe depicts the orientation of the sensor holder with respect to the shear tie. Also shown in a diagram of the transducer recesses for the transmitting and receiving inspection sensors is the 0.125 inch vertical separation for the transducer recesses.

For each of the frame inspection diagrams it is also noted that the flanges are oriented upward although this may not be required due to the clam-like operation of the inspection sensor. And the shear tie inspection diagram notes that the flanges are oriented downward, which may be typical where gravity is used to ensure contact for the inspection probe to ride along the shear tie, but may not be required if an alternative control and/or pressure force is provided, such as manual operation of a shear tie radius probe by an operator located beneath an upwardly pointing flange.

The diagram 402 also depicts the components of the portable function support system. A computer 450 with attached monitor 451, keyboard 452, and mouse 453 is shown connected by Ethernet connections to a PEU inspection system 458, a General Electric USIP40 10 channel pulser/receiver, and to a TTU inspection system 470, a thirty-two channel multiplexed TTU inspection system as described in application Ser. No. 11/178,584. The PEU inspection system 458 is connected to a shear tie radius PE probe 460 by five coaxial cables for PE data and an encoder channel for position data. The TTU inspection system 470 is connected to a flange TTU probe 462, a web TTU probe 464, and a radius TTU probe 466. Each of these frame TTU probes are connected by multiple channels for transmit and receive TTU inspection data and an encoder channel through a breakout connector box 468 connected to the TTU inspection system 470. Because only one encoder circuit may be provided, such as in the thirty-two channel TTU electronics of FIG. 37, an encoder switch circuit 480 may be used to select an encoder of a single probe and the direction of travel for the probe, such as to select a fuselage frame flange, web, or radius probe and direction along the fuselage frame of phase A or phase B.

A water pump 482 is shown connected by water feed tubes to all four of the inspection probes through a fluid flow manifold 484 with four valves, one controlling flow to each of the four inspection probes. A fluid manifold and water pump may be controlled manually or may be controlled electronically, such as by computer control in which case a connection between the computer 450 and the water pump 482 and/or fluid manifold 484 may be required.

The diagram 402 also depicts at the bottom left a frame display window 430 showing the orientation for display of the cumulative results and analysis of the inspection data for a fuselage frame. The diagram shows that inboard data 432 is presented beginning with the inboard flange, followed by the inboard radius, and followed by the inboard web. The inboard data 432 is followed by the outboard data 434 which is presented beginning with the outboard web (adjacent the inboard web data), followed by the outboard radius, and followed by the outboard flange. As such, the display of the flange provides a visual representation of the structure of the U-shaped frame, and features thereof with respect to each other as they exist in a physical form. Similarly, the diagram 402 also depicts at the bottom right a shear tie display window 440 showing the orientation for display of the cumulative results and analysis of the inspection data for a fuselage shear tie.

As discussed herein, and also as discussed in application Ser. Nos. 11/368,557, 11/213,652, 11/178,584, 11/178,637, 10/943,088, application Ser. No. 10/943,135, and Ser. No. 11/041,499, one or more computer programs, i.e., software, operating on a computer or other hardware and software system with a processor capable of operating under software control, such as the computer 450 of the portable function support system, may be used for data acquisition of ultrasonic inspection data transmitted from ultrasonic receiver or transceiver transducers to a receiving device, such as through a multi-channel multiplexed TTU inspection system or PEU inspection system, and related or combined software may also be used to analyze the received data. Such a software program is provided by the Data Acquisition and Analysis Software (DAAS) program as depicted in FIGS. 38 and 39. Data analysis software interprets the inspection data and maps a C-scan from the probe onto a display for review by an operator, such as a technician performing a manual scanning operation. For example, the software may combine the inspection data from ultrasonic transducers with position data from an optical encoder with predefined structural data representing the configuration of the structure under inspection, including any position information for discontinuities in the structure such as found on a fuselage shear tie, to provide the technician a virtual image of the ongoing non-destructive inspection by the ultrasonic inspection system. Data analysis software may also provide a user with tools for further controlled analysis of the displayed data.

FIG. 38 is a graphical user interface display for operating with the portable function support system of FIG. 35 to perform fuselage frame inspection. The software display provides a user with a relative visual representation of the U-shaped frame as described above with respect to the frame display window 430. As such, the underlying analysis software is capable of proving a display where the user can visually identify corresponding inspection of adjacent portions of the same structure using separate inspection probes, and typically from inspection data obtained during non-simultaneous inspection operations. Positional data from encoders on the probes may be used to coordinate the inspection data to relative positions on the same structure under inspection, such as at the same relative point about the circumference of a structure or at the same relative point about the length of a structure. FIG. 39 is another graphical user interface display for operating with the portable function support system of FIG. 35 to perform fuselage shear tie inspection.

Computer program instructions for software control for embodiments of the present invention may be loaded onto a computer or other programmable apparatus to produce a machine, such that the instructions which execute on the computer or other programmable apparatus create means for implementing the functions described herein. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions described herein. It will also be understood that each step, and combinations of steps, can be implemented by hardware-based computer systems, software computer program instructions, or combinations of hardware and software which perform the specified functions or steps for facilitating inspection with embodiments of inspection probes and portable function support system in accordance with the present invention.

As described above, an embodiment of the present invention may use a multi-channel multiplexed inspection system as disclosed more fully in application Ser. No. 10/949,625. As such, FIG. 40 is a schematic block diagram of a thirty-two channel multiplexed TTU inspection system of the kind which may be used with an embodiment of the present invention. Specifically, system 600 includes thirty-two pairs of corresponding transducers. Of the sixty-four transducers, thirty-two transducers are transmitting transducers 610 or pulsing transducers on one side of a component or structure (for example, fuselage frame shown in FIG. 1 or fuselage shear tie shown in FIG. 2) under inspection. The other thirty-two transducers are receiving transducers 612 on the opposing side of the structure under inspection. Thus, thirty-two channels are provided for thirty-two transmit transducers 610 and thirty-two channels are provided for thirty-two receive transducers 610. As used herein, a "channel" refers to the communication link to a transducer. The transducers may be included in one device or probe. Alternatively, the plurality of channels may be divided in such a manner as to function as an array of probes, such as a sixty-four probe array with thirty-two transmitting probes and thirty-two receiving probes, where each probe includes one transducer. Or, for example, a thirty-two channel multiplexer inspection system may be divided into twelve channels for a fuselage frame flange probe, fifteen channels for a fuselage frame web probe, and three channels for a fuselage frame radius probe. Each transmit or receive channel corresponds with an individual piezoelectric crystal transducer. The individual transducers, as described, may be arranged as in a single probe or a number of probes functioning in an array.

Each of the thirty-two transmit channels 610 may be sequentially pulsed, such as a pulser board pulsing channels 1 through thirty-two, one channel every 200 microseconds (µs), at a 5 kHz repetition rate to cycle through the thirty-two channels 610 once every 6.4 milliseconds (ms). A pulser board pulsing channels refers to the pulser board providing a transmit signal to a transmit channel for a transducer. An example pulser board, or interface board or receiver board, may be a printed circuit board (PCB) with electrical connections or communication paths. The interface board 614, and/or a processor or microcontroller of an attached computer (not shown), may be used to control the sequential pulsing of the thirty-two transmit channels 610 and coordination of the sequence of received signals. The repetition rate for the cycling of channels is typically selected, and limited, in part due to the time for an ultrasonic signal to propagate from a transmitting transducer crystal through a couplant to the surface of the part, through the part under inspection, and from the surface of the part through a couplant to a receiving transducer crystal. The repetition rate may also be dependent upon such factors as the communication bandwidth to transmit the processed signals from the multiplexing receiver board to a computer controlling and/or processing the inspection.

The embodiment of the present invention shown in FIG. 40 shows two sixteen channel pulser boards 620, 622, each connected to an interface board 614 and each providing sixteen of the thirty-two transmit channels 610. A pulser board typically is a PCB board which can independently provide signals intended for the sixteen different transducers from an interface board to the sixteen corresponding channels using corresponding pulsers of the pulser board which provide electronic pulse signals for the digital or electronic signals from the interface board. Also included are two sixteen channel receiver boards or RF amplifier and A/D boards 624, 626, each coupled to the interface board 614 and each receiving sixteen of the thirty-two receive channels 12.

A thirty-two channel multiplexed TTU system as shown in FIG. 40 may also include an encoder interface 616 to provide an interface between positional encoders 618 of a scanning system and an interface board 614 of the thirty-two channel multiplexed TTU system. An encoder interface 616 may include two counter chips, such as LS7266R1 counter chips manufactured by LSI Computer Systems, Inc., of Melville, N.Y. The counter chips have internal registers which hold the current value as an encoder on the scanning system moves back and forth with a scanning probe. The counter chips will count up and down from a reference value to provide different values for the internal registers of the counter chips. This information is typically referred to as position information of the scanning system. The position information is relative to the position of the transducers in some physical manner because the encoders are mechanically tracking the movement of the transducers. Thus, the position information provided by an encoder is synchronous to the movement of a scanning probe, but the transducer signals are asynchronous to the scanner movement. Thus by combining the position information of the encoder through an encoder interface, a microprocessor is capable of tying the two pieces of information together to establish the position of a transducer for a particular ultrasonic signal. For example, a microprocessor may combine positional information from the counter chips of the encoder interface into the same data packet as the corresponding ultrasonic data. Additional software may then be able to analyze the particular data packet as having an ultrasonic data value at a specific position which occurred during the scan.

A receiver board 624, 626 may include a tuned filter 702 for each receive channel 612. For example, a tuned filter 702 may include a base amplifier and a tank circuit. A tunable capacitor of a tuned filter 702 may be adjusted to filter the received signal to a specific frequency, such the frequency of a piezoelectric crystal oscillating at 5 MHz. After filtering each of the received signals, all sixteen signals are provided to a first layer of multiplexing switches 706, referred to as a first multiplexing chip. As a non-limiting example, a multiplexing chip may be a MAX310CPE multiplexing chip manufactured by Maxim Integrated Products, Inc., of Sunnyvale, Calif., which permits a signal voltage input range of 15 volts peak-to-peak (Vpp). The first layer of multiplexing switches 706 may provide 60 dB of isolation between the sixteen signals. A second layer of multiplexing switches 708, also referred to as a second multiplexing switch may provide an additional 10 dB of isolation between the channels. The second layer of multiplexing switches 708 may also use MAX310CPE multiplexing switches. Using two layers of multiplexing switches 708 can achieve 70 dB of isolation between the channels. With 70 dB of isolation between channels, one channel can be 3000 times greater than another channel without affecting the smaller input as provided by 70 dB=20×Log(difference) where (difference) is equal to 3000 for 70 dB. For example, one channel can have a 5 MHz signal with a strength of 1 millivolt (mV) and another channel can have a 5 MHz signal with a 3 volt (V) strength without affecting the 1 mV signal. Also, by separating the multiplexing switches into two layers, the capacitance is decreased so as not to degrade the RF signal. Different combinations of channel switching may be used with the two layers of multiplexing switches. For example, a single 60 dB multiplexing chip used to switch between sixteen channels may be used with two 10 dB multiplexing chips to switch between 8 channels each. By selecting corresponding channels in the first layer of multiplexing switches 706 and the second layer of multiplexing switches 708, a single receive channel may be selected.

The single receive channel signal, filtered and multiplexed, is provided to a logarithmic amplifier 710 which provides logarithmic amplification for 70 dB of dynamic range, such as a voltage range of −67 dB to +3 dB, although logarithmic amplification can be centered around different dynamic ranges. Thus, the layered multiplexing chips 706, 708 provide the full dynamic range of the capabilities of the logarithmic amplifier 710. Logarithmic amplification follows the formula $Gain_{log}=20 \times Log(V_{out}/V_{in})$. After logarithmic amplification, the signal may be linearly amplified by a linear amplifier 714, such as to provide 20 dB of linear amplification to adjust the logarithmically amplified signal to the full range of an analog to digital converter. Linear amplification follows the formula $Gain_{lin}=(V_{out}/V_{in})$. The signal may then be converted from analog to digital using an analog to digital chip 718 (A/D converter), such as an analog to digital chip with an input of 0 to 10 volts. An envelope (peak) detector 716 and a diode 715 may be used between the linear amplification and the conversion from analog to digital such that the peak value is converted to a digital signal by the A/D converter. The diode 715 can isolate the positive voltage of the amplified signal to permit the envelope (peak) detector 716 to capture the peak amplitude of the signal. Only the peak amplitudes of a signal are required for TTU inspection to identify flaws from changing amplitudes. For example, the logarithmic amplifier 710 may output a signal with 1.4 volts peak-to-peak (Vpp) centered around 0 volts; the linear amplifier 714 may increase the signal to a 20 Vpp signal (−10 V to +10 V); the diode 715 may isolate the +10 V peak range (0 V to +10 V); the envelope peak detector 716 may capture the peak amplitudes of the signal ranging from 0 V to +10 V; and the analog to digital chip 718 may convert the 0 to 10 V signal to a digital signal with a 12 bit resolution.

The use of the large 70 dB dynamic range logarithmic amplification assists in the identification of small changes or imperfections in a part under inspection. For example, 70 dB of dynamic range may be required to find a piece of foreign material located sixty-eight plys (layers) down in a half inch thick piece of graphite under inspection, where one ply, or one layer, is seven thousandths of an inch thick. The foreign piece of material may be almost on the bottom edge of the piece of graphite under inspection as viewed through the part from the transmitting transducer to the receiving transducer. Sound, or specifically an ultrasonic signal, diminishes as it propagates through a part under inspection.

For example, in the inspection of the half inch thick piece of graphite, the ultrasonic signal may have dropped by as much as 60 dB in through transmission before it reaches the sixty-eighth ply where the piece of foreign material is located and for which 2 dB of change may be necessary to detect the presence of the piece of foreign material. In order to detect the 2 dB of change, the noise must not be so great as to mask the 2 dB change for the piece of foreign material. The dynamic range must be large enough to detect the flaw in the structure under inspection, the piece of foreign material in the graphite. By using a large logarithmic gain, a scanning system may be capable of resolving a high level of detail in a part under inspection. Using logarithmic amplification amplifies the small changes more than large changes in the signal. Typically, large changes in a signal include noise. By comparison, when using linear amplification, the noise is amplified just as much as the signal. And by using a large dynamic range, a system is capable of scanning thick parts.

In addition to accounting for a high dynamic range, the system must be able to multiplex the high dynamic range without acquiring crosstalk, or noise between the channels. To switch or multiplex the large dynamic range signals without introducing noise or crosstalk between the channels, the multiplexing may be performed by layering multiplexing chips, such as described by using an initial 60 dB range and a second layer of 10 dB range multiplexing chips.

FIG. 41 is a schematic block diagram of a thirty-two channel multiplexed TTU inspection system 600 connected to a remote processor using an Ethernet connection. As may be seen in the schematic diagram of FIG. 41, thirty-two transmit channels 610 may be coupled to thirty-two transducers which are used to inspect a part 630. Thirty-two receive channels 612 may be coupled to thirty-two receive transducers to receive signals transmitted through a part under inspection 630 from thirty-two corresponding transmitting transducers. The multiplexed TTU system may be connected to a remote processor 642, such as a computer with a microprocessor for further processing, analyzing, and displaying results of the inspection, through a communication connection or a link, such as an Ethernet communication connection 640 or a serial communication connection, as described more fully herein. Communication connections, such as Universal Serial Bus (USB) and Bluetooth (BT) technologies may be use with embodiments of the present invention.

As previously described, embodiments of the present invention may be used in manual scanning operations, such as where an operator slides an inspection device along a structure, or may be used in semi-automated or automated scanning operations. Also, as previously mentioned, sensor holders of embodiments of the present invention may be made in various configurations to conform to equally varying configurations of structures to be scanned using inspection sensors for through transmission and pulse echo ultrasonic inspection operations. Use of multi-channel multiplexed inspection systems facilitates the collective and cooperative inspection with different inspection probes. And use of positional feedback and visual display interfaces provides a user with the ability to see the inspection results as rapidly as the analysis is performed during the inspection operation. Implementing a function support system, such as described as including a multi-channel multiplexed inspection system, in a portable (moveable) configuration permits the ability to rapidly inspect large composite structures, potentially having awkward structural features and characteristics without the added complexity of fixed motion control hardware, large immersion tanks, and the like. Function support systems as described herein may be capable of implementing real-time inspection, data capture, and analysis of between 8 and 10 inches per second.

Embodiments of the present invention provide apparatus, systems, and methods for ultrasonic inspection of uniquely shaped structures such as fuselage frames and shear ties. Probes may be constructed from rapid prototyping. Inspection may use a portable function support system for delivering fluid couplant, controlling transmit and receive functions of the inspection sensors, and delivering immediate visual analysis for an operator. Integrated ultrasonic inspection apparatus, systems, and methods facilitate fast and efficient custom inspection devices and inspecting otherwise difficult-to-inspect structures.

The invention should not be limited to the specific disclosed embodiments and modifications and other embodiments of the invention are intended to be included within the scope of the appended claims. Specific terms are used in a generic and descriptive sense only and not for purposes of limitation.

That which is claimed:

1. A method of non-destructive inspection, comprising:
    supporting at least a first part of an inspection device and a second part of an inspection device on both a first portion of a structure and a second portion of the structure, wherein the first portion of the structure and the second portion of the structure are defined with a radius therebetween, wherein the first part is configured to pass over at least a first surface of the first portion of the structure and a first surface of the second portion of the structure, wherein the second part is configured to pass over at least a second surface of the first portion of the structure and a second surface of the second portion of the structure, wherein the first and second surfaces of the first portion of the structure are opposing surfaces, wherein the first and second surfaces of the second portion of the structure are opposing surfaces, wherein the first part comprises a first sensor holder defining a first recess for supporting and orienting a first ultrasonic inspection sensor at least partially disposed within the first recess and configured to inspect at least the first portion of the structure as the first and second parts of the inspection device are passed over at least the first portion of the structure and the second portion of the structure;
    passing the first part of the inspection device over at least the first surface of the first portion of the structure and the first surface of the second portion of the structure;
    passing the second part of the inspection device over at least the second surface of the first portion of the structure and the second surface of the second portion of the structure; and
    transmitting ultrasonic signals from the first ultrasonic inspection sensor to at least the first portion of the structure.

2. The method of claim 1, wherein the second part comprises a second sensor holder defining a second recess for supporting and orienting a second ultrasonic inspection sensor at least partially disposed within the second recess and configured to inspect at least the first portion of the structure as the first and second parts of the inspection device are passed over at least the first portion of the structure and the second portion of the structure; and
    further comprising receiving the ultrasonic signals, transmitted from the first ultrasonic inspection sensor and propagated through the first portion of the structure, at the second ultrasonic inspection sensor, wherein the inspection device is configured to maintain the first ultrasonic inspection sensor and the second ultrasonic inspection sensor in proper alignment and spacing to permit the second ultrasonic inspection sensor to receive the ultrasonic signals transmitted from the first ultrasonic inspection sensor and propagated through the first portion of the structure.

3. The method of claim 2, wherein the inspection device is configured to inspect at least one of a fuselage frame flange and a fuselage frame web.

4. The method of claim 2, wherein the inspection device is further configured to pull the second sensor holder against the second surface of the first portion of the structure.

5. The method of claim 1, wherein the inspection device is configured to inspect a plurality of structures having radii of different sizes between the first portion of the structure and the second portion of the structure.

6. The method of claim 1, further comprising selecting a predefined structure in a computer program corresponding to the structure to be inspected by the inspection device.

7. The method of claim 1, further comprising selecting a predefined inspection device in a computer program corresponding to the inspection device to be used to inspect the structure.

8. The method of claim 1, wherein the first ultrasonic inspection sensor is a linear inspection sensor, and wherein transmitting ultrasonic signals from the first ultrasonic inspection sensor comprises transmitting ultrasonic signals over a planar length of the first ultrasonic inspection sensor.

9. The method of claim 1, wherein the first ultrasonic inspection sensor is a linear inspection sensor, and wherein transmitting ultrasonic signals from the first ultrasonic inspection sensor comprises transmitting ultrasonic signals in parallel through a plane, wherein the plane is parallel to the first portion of the structure.

10. The method of claim 9, wherein the first portion of the structure comprises a flat surface.

11. The method of claim 1, further comprising receiving the ultrasonic signals, transmitted from the first ultrasonic inspection and reflected from the first portion of the structure, at the first ultrasonic inspection sensor.

12. A method of non-destructive inspection, comprising:
    supporting at least a first part of an inspection device on both a first portion of a structure and a second portion of the structure, wherein the first portion of the structure and the second portion of the structure are defined with a radius therebetween, wherein the first part is configured to pass over at least a first surface of the first portion of the structure, a first surface of the second portion of the structure, and a first surface of the radius between the first and second portions of the structure, wherein a second part of the inspection device is configured to pass over at least a second surface of the first portion of the structure and a second surface of the second portion of the structure, wherein the first and second surfaces of the first portion of the structure are opposing surfaces, wherein the first and second surfaces of the second portion of the structure are opposing surfaces, wherein the first part comprises a first sensor holder defining a first recess for supporting and orienting a first ultrasonic inspection sensor at least partially disposed within the first recess and configured to inspect at least the first portion of the structure as the first and second parts of the inspection device are passed over the first portion of the structure, the second portion of the structure, and the radius between the first and second portions of the structure;

passing the first part of the inspection device over the first surface of the first portion of the structure, the first surface of the second portion of the structure, and the first surface of the radius between the first and second portions of the structure;

passing the second part of the inspection device over the second surface of the first portion of the structure and the second surface of the second portion of the structure; and transmitting ultrasonic signals from the first ultrasonic inspection sensor to at least the first portion of the structure.

13. The method of claim 12, wherein the second part comprises a second sensor holder defining a second recess for supporting and orienting a second ultrasonic inspection sensor at least partially disposed within the second recess and configured to inspect at least the first portion of the structure as the first and second parts of the inspection device are passed over at least the first portion of the structure and the second portion of the structure; and further comprising receiving the ultrasonic signals, transmitted from the first ultrasonic inspection sensor and propagated through the first portion of the structure, at the second ultrasonic inspection sensor, wherein the inspection device is configured to maintain the first ultrasonic inspection sensor and the second ultrasonic inspection sensor in proper alignment and spacing to permit the second ultrasonic inspection sensor to receive the ultrasonic signals transmitted from the first ultrasonic inspection sensor and propagated through the first portion of the structure.

14. The method of claim 13, wherein the inspection device is configured to inspect at least one of a fuselage frame flange and a fuselage frame web.

15. The method of claim 13, wherein the inspection device is further configured to pull the second sensor holder against the second surface of the first portion of the structure.

16. The method of claim 13, wherein the first sensor holder further defines a third recess for supporting and orienting a third ultrasonic inspection sensor at least partially disposed within the third recess and configured to inspect the radius between the first portion of the structure and the second portion of the structure as the first and second parts of the inspection device are passed over at least the first portion of the structure, the second portion of the structure, and the radius between the first and second portions of the structure, wherein the second sensor holder further defines a fourth recess for supporting and orienting a fourth ultrasonic inspection sensor at least partially disposed within the fourth recess and configured to inspect the radius between the first portion of the structure and the second portion of the structure as the first and second parts of the inspection device are passed over at least the first portion of the structure, the second portion of the structure, and the radius between the first and second portions of the structure, wherein the third recess and the fourth recess are radially directed at the radius; and further comprising:

transmitting ultrasonic signals from the third ultrasonic inspection sensor to the radius between the first and second portions of the structure; and receiving the ultrasonic signals, transmitted from the third ultrasonic inspection sensor and propagated through the radius between the first and second portions of the structure, at the fourth ultrasonic inspection sensor, wherein the inspection device is configured to maintain the third ultrasonic inspection sensor and the fourth ultrasonic inspection sensor in proper alignment and spacing to permit the fourth ultrasonic inspection sensor to receive the ultrasonic signals transmitted from the third ultrasonic inspection sensor and propagated through the radius between the first and second portions of the structure.

17. The method of claim 16, wherein the inspection device is further configured to maintain the third ultrasonic inspection sensor and the fourth ultrasonic inspection sensor at a fixed separation spacing.

18. The method of claim 12, wherein the inspection device is configured to inspect a plurality of structures having radii of different sizes between the first portion of the structure and the second portion of the structure.

19. The method of claim 12, further comprising selecting a predefined structure in a computer program corresponding to the structure to be inspected by the inspection device.

20. The method of claim 12, further comprising selecting a predefined inspection device in a computer program corresponding to the inspection device to be used to inspect the structure.

21. The method of claim 12, wherein the first ultrasonic inspection sensor is a linear inspection sensor, and wherein transmitting ultrasonic signals from the first ultrasonic inspection sensor comprises transmitting ultrasonic signals over a planar length of the first ultrasonic inspection sensor.

22. The method of claim 12, wherein the first ultrasonic inspection sensor is a linear inspection sensor, and wherein transmitting ultrasonic signals from the first ultrasonic inspection sensor comprises transmitting ultrasonic signals in parallel through a plane, wherein the plane is parallel to the first portion of the structure.

23. The method of claim 22, wherein the first portion of the structure comprises a flat surface.

24. The method of claim 12, further comprising receiving the ultrasonic signals, transmitted from the first ultrasonic inspection and reflected from the first portion of the structure, at the first ultrasonic inspection sensor.

25. The method of claim 12, wherein the first part further comprises a first wing appendage for supporting the first part of the inspection device on the first portion of the structure, and wherein supporting the first part of the inspection device on the first portion of the structure comprises supporting the first wing appendage against the first portion of the structure.

26. The method of claim 25, wherein the first part further comprises a second wing appendage for supporting the first part of the inspection device on the second portion of the structure, and wherein supporting the first part of the inspection device on the second portion of the structure comprises supporting the second wing appendage against the second portion of the structure.

27. The method of claim 25, wherein the second part further comprises a second wing appendage for supporting the second part of the inspection device on the first portion of the structure, and wherein supporting the second part of the inspection device on the first portion of the structure comprises supporting the second wing appendage against the first portion of the structure.

28. A method of non-destructive inspection, comprising:

supporting an inspection device on both a first portion of a structure and a second portion of the structure, wherein the first portion of the structure and the second portion of the structure are defined with a radius therebetween, wherein the inspection device is configured to pass over the first portion of the structure, the second portion of the structure, and the radius between the first and second portions of the structure, wherein the inspection device comprises a sensor holder defining a first recess for supporting and orienting a first ultrasonic inspection sensor at least partially disposed within the recess and configured to inspect the radius between the first and second portions of the structure as the inspection device is passed over the first portion of the structure, the second portion of the structure, and the radius between the first and second portions of the structure, wherein the first recess is radially directed at the radius between the first and second portions of the structure;

passing the inspection device over the first portion of the structure, the second portion of the structure, and the radius between the first and second portions of the structure;

transmitting ultrasonic signals from the first ultrasonic inspection sensor to at least the radius between the first and second portions of the structure; and receiving the ultrasonic signals, transmitted from the first ultrasonic inspection and reflected from the radius between the first and second portions of the structure, at the first ultrasonic inspection sensor.

29. The method of claim 28, wherein the inspection device is configured to inspect a fuselage shear tie.

30. The method of claim 28, further comprising selecting a predefined structure in a computer program corresponding to the structure to be inspected by the inspection device.

31. The method of claim 28, further comprising selecting a predefined inspection device in a computer program corresponding to the inspection device to be used to inspect the structure.

32. The method of claim 28, wherein the first ultrasonic inspection sensor is a curved linear inspection sensor, and wherein transmitting ultrasonic signals from the first ultrasonic inspection sensor comprises transmitting ultrasonic signals at an angle through a plane, wherein the plane is a tangent to the radius between the first and second portions of the structure.

33. The method of claim 32, wherein transmitting ultrasonic signals at an angle through a plane comprises transmitting ultrasonic signals converging in the direction of a convex surface of the radius between the first and second portions of the structure.

34. The method of claim 32, wherein transmitting ultrasonic signals at an angle through a plane comprises transmitting ultrasonic signals diverging in the direction of a concave surface of the radius between the first and second portions of the structure.

35. The method of claim 28, wherein the inspection device further comprises a first wing appendage for supporting the inspection device on the first portion of the structure, and wherein supporting the inspection device on the first portion of the structure comprises supporting the first wing appendage against the first portion of the structure.

36. The method of claim 35, wherein the inspection device further comprises a second wing appendage for supporting the inspection device on the second portion of the structure, and wherein supporting the inspection device on the second portion of the structure comprises supporting the second wing appendage against the second portion of the structure.

* * * * *